(12) United States Patent
Ishii et al.

(10) Patent No.: US 11,300,998 B2
(45) Date of Patent: Apr. 12, 2022

(54) WEARABLE DEVICE TO STIMULATE SENSE ORGANS IN THE SKIN OF A USER, WEARABLE DEVICE SYSTEM, AND METHOD FOR CONTROLLING WEARABLE DEVICE

(71) Applicant: KYOCERA CORPORATION, Kyoto (JP)

(72) Inventors: Atsushi Ishii, Yokohama (JP); Tadamichi Nishikawa, Yokohama (JP)

(73) Assignee: Kyocera Corporation, Kyoto (JP)

( * ) Notice: Subject to any disclaimer, the term of this patent is extended or adjusted under 35 U.S.C. 154(b) by 607 days.

(21) Appl. No.: 16/305,013

(22) PCT Filed: May 24, 2017

(86) PCT No.: PCT/JP2017/019316
§ 371 (c)(1),
(2) Date: Nov. 27, 2018

(87) PCT Pub. No.: WO2017/204242
PCT Pub. Date: Nov. 30, 2017

(65) Prior Publication Data
US 2021/0223817 A1    Jul. 22, 2021

(30) Foreign Application Priority Data
May 27, 2016    (JP) .............................. JP2016-106135

(51) Int. Cl.
*G06F 1/16*    (2006.01)
*G06F 3/01*    (2006.01)

(52) U.S. Cl.
CPC .............. *G06F 1/163* (2013.01); *G06F 3/014* (2013.01); *G06F 3/016* (2013.01)

(58) Field of Classification Search
CPC ........... G06F 1/163; G06F 3/014; G06F 3/016
See application file for complete search history.

(56) References Cited

U.S. PATENT DOCUMENTS

| 10,275,143 | B2 * | 4/2019 | Nagaraju | ................ | G06F 3/016 |
| 2013/0222280 | A1 * | 8/2013 | Sheynblat | ............... | G06F 3/016 |
| | | | | | 345/173 |
| 2014/0247132 | A1 * | 9/2014 | Fukuma | ............... | H05B 47/155 |
| | | | | | 340/815.45 |
| 2018/0081439 | A1 * | 3/2018 | Daniels | ................... | G06F 3/015 |

FOREIGN PATENT DOCUMENTS

| JP | 2007-143812 A | | 6/2007 |
| JP | 2015-503173 A | | 1/2015 |
| JP | 2016-051319 A | | 4/2016 |
| JP | 2016051319 A | * | 4/2016 |
| WO | 2013/073437 A1 | | 5/2013 |

* cited by examiner

*Primary Examiner* — Laurence J Lee
(74) *Attorney, Agent, or Firm* — Duane Morris LLP

(57) ABSTRACT

A wearable apparatus comprises a first communication unit, a stimulator, and a first processor. The first communication unit receives first information based on a physical quantity. The stimulator stimulates sense organs in the skin of the first user by a controllable stimulation quantity. The first processor causes the stimulator to stimulate the sense organs based on the first information so that the physical quantity is reproduced on the sense organs.

14 Claims, 21 Drawing Sheets

WEARABLE DEVICE TO STIMULATE SENSE ORGANS IN THE SKIN OF A USER, WEARABLE DEVICE SYSTEM, AND METHOD FOR CONTROLLING WEARABLE DEVICE

CROSS-REFERENCE TO RELATED APPLICATION

The present application is a National Phase entry based on PCT Application No. PCT/JP2017/019316 filed on May 24, 2017, entitled "WEARABLE DEVICE, WEARABLE DEVICE SYSTEM, AND METHOD FOR CONTROLLING WEARABLE DEVICE" which claims the benefit of Japanese Patent Application No. 2016-106135, filed on May 27, 2016, entitled "WEARABLE APPARATUS, WEARABLE APPARATUS SYSTEM, METHOD FOR CONTROLLING WEARABLE APPARATUS, DEVICE FOR CONTROLLING WEARABLE APPARATUS AND CONTROL PROGRAM", the contents of which are incorporated by reference herein in their entirety.

FIELD

The present disclosure relates to a wearable apparatus, a wearable apparatus system, and a method for controlling the wearable apparatus.

Background

Various technologies on wearable apparatuses have been conventionally proposed.

SUMMARY

A wearable apparatus, a wearable apparatus system, and a method for controlling the wearable apparatus will be disclosed. The wearable apparatus comprises a first communication unit, a stimulator, and a first processor. The first communication unit receives first information based on a physical quantity. The stimulator stimulates sense organs in the skin of the first user by a controllable stimulation quantity. The first processor causes the stimulator to stimulate the sense organs based on the first information so that the physical quantity is reproduced on the sense organs.

In another embodiment, a wearable apparatus system comprises a first wearable apparatus and a second wearable apparatus that can communicate with each other. The first wearable apparatus comprises a sensor. The sensor detects a physical quantity. The second wearable apparatus comprises a stimulator and a processor. The stimulator stimulates sense organs of a user by a controllable stimulation quantity. The processor causes the stimulator to stimulate the sense organs so that the physical quantity is reproduced on the sense organs.

In yet another embodiment, a method for controlling a wearable apparatus comprises first and second processes. The first process is receiving first information based on a physical quantity. The second process is causing a stimulator to stimulate sense organs of a user based on the first information so that the physical quantity is reproduced on the sense organs.

DETAILED DESCRIPTION

[Appearance of Electronic Apparatus]

Figure 1:
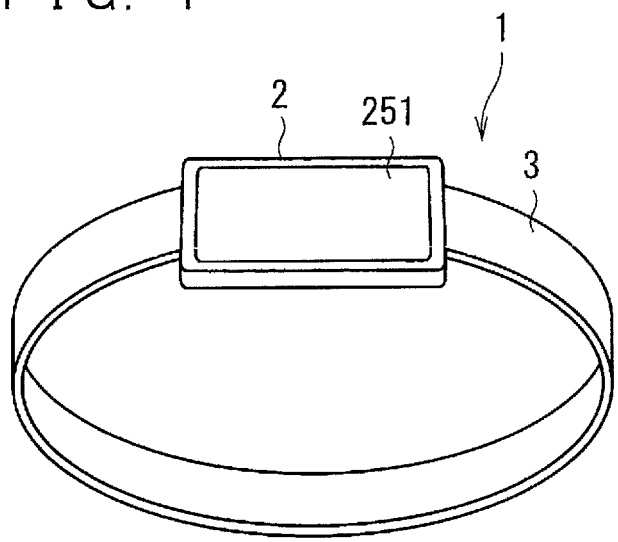
FIG. 1 illustrates a perspective view schematically showing one example appearance of a wearable apparatus.

FIG. 1 illustrates a perspective view schematically showing one example appearance of a wearable apparatus 1. This wearable apparatus 1 is worn on a user. FIG. 1 exemplifies a bracelet-type apparatus as the wearable apparatus 1. The wearable apparatus 1 is not necessarily limited to this. The wearable apparatus 1 may be any of wearable apparatuses of, for example, finger ring type, earphone type, and headphone type. One example where the wearable apparatus 1 is a bracelet-type apparatus will be hereinafter described.

FIG. 1 exemplifies that the wearable apparatus 1 comprises a main body 2 and a band part 3. The band part 3 is a plate-shaped strip both ends of which are attached to the main body 2. Accordingly, the wearable apparatus 1 is ring-shaped. The user can wear the wearable apparatus 1 by fitting the band part 3 of the wearable apparatus 1 on the arm.

The main body 2 accommodates a mechanical configuration and an electrical configuration to be described later. The main body 2 may be, for example, flat plate-shaped. As exemplified in FIG. 1, the main body 2 may be, for example, rectangular plate-shaped.

As exemplified in FIG. 1, the main body 2 may have, on the outer peripheral surface, for example a display area 251. A display 25 to be described later displays various information on this display area 251. The user can know the various information by visually recognizing this display area 251. The display 25 may display, for example, time on the display area 251. If the display 25 displays time, the wearable apparatus 1 functions as a generally-called watch.

[Outline of System]

Figure 2:
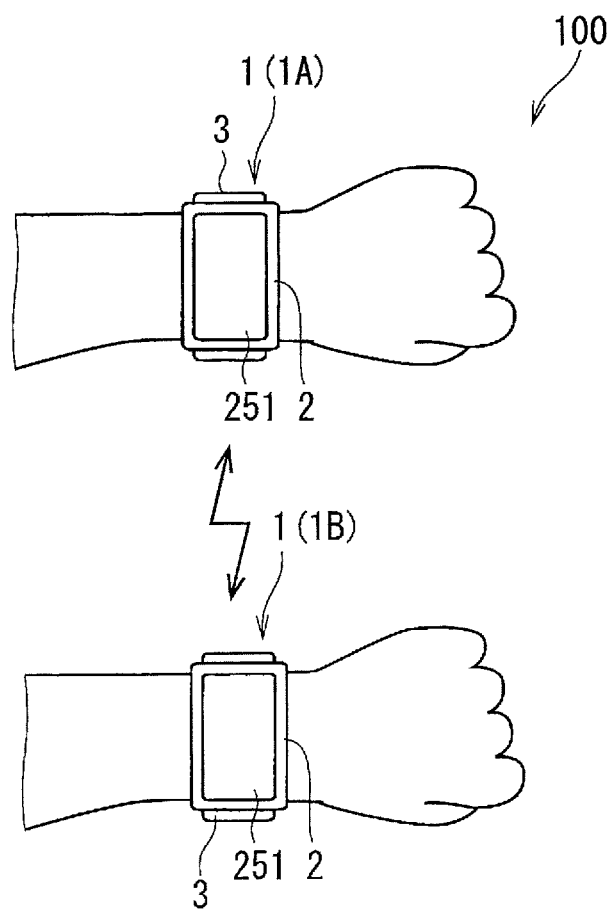
FIG. 2 schematically illustrates one example structure of a wearable apparatus system.

FIG. 2 schematically illustrates one example structure of a wearable apparatus system 100. As exemplified in FIG. 2, the wearable apparatus system 100 comprises a plurality of wearable apparatuses 1. FIG. 2 exemplifies the two wearable apparatuses 1. These wearable apparatuses 1 can communicate with each other. The wearable apparatuses 1 may communicate with each other directly or through an external apparatus that is not illustrated (e.g., at least one of a base station, a server, and a mobile apparatus such as a smartphone).

These two wearable apparatuses 1 may be referred to as wearable apparatuses 1A and 1B to be distinguished from each other. The wearable apparatus 1A is worn on a user UA, and the wearable apparatus 1B is worn on a user UB. FIG. 2 exemplifies that the wearable apparatuses 1A and 1B are worn on the arms (for example, wrists) of the users UA and UB, respectively.

[Electrical Configuration of Wearable Apparatus]

Figure 3:
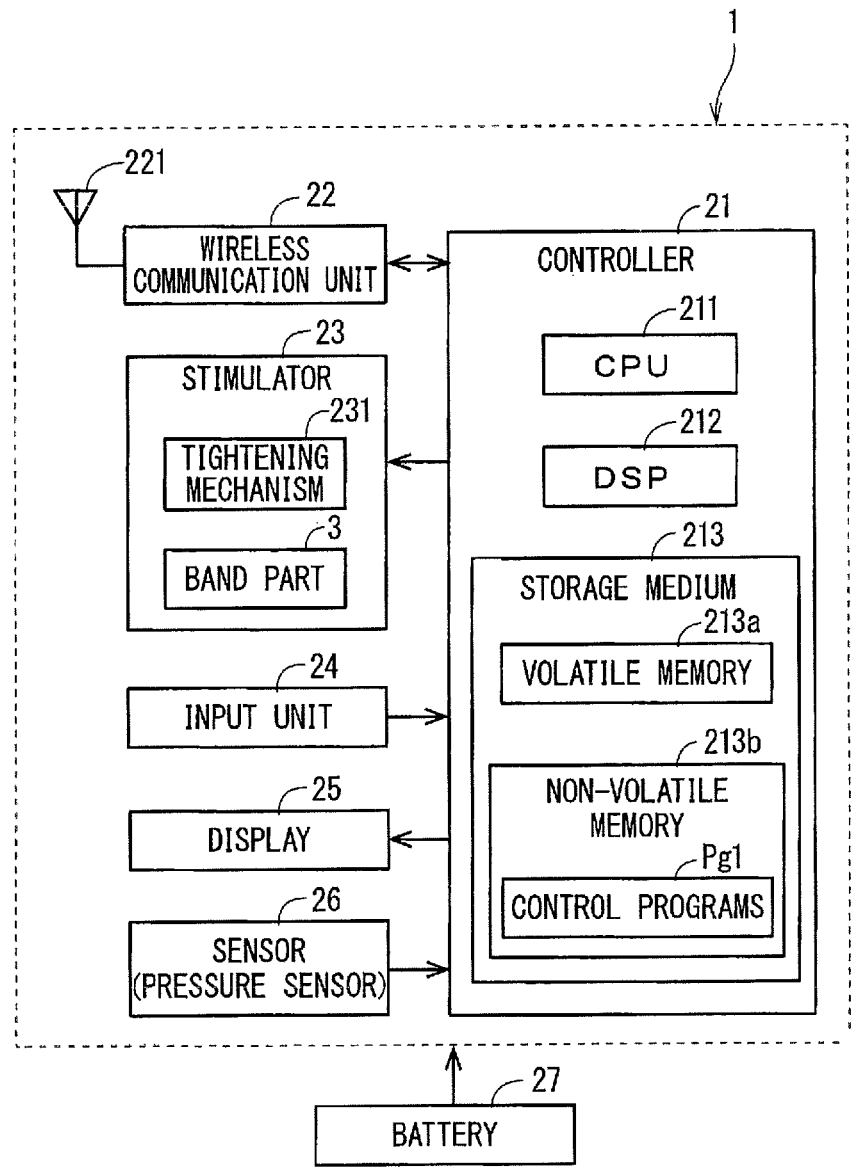
FIG. 3 illustrates a functional block diagram schematically showing one example electrical configuration of a wearable apparatus.

FIG. 3 illustrates a functional block diagram schematically showing one example electrical configuration of the wearable apparatus 1. The wearable apparatus 1 comprises a controller 21, a wireless communication unit 22, a stimulator 23, an input unit 24, the display 25, a sensor 26, and a battery 27.

The controller 21 is housed in, for example, the main body 2. This controller 21 can manage overall operations of the wearable apparatus 1 by controlling the other constituent elements of the wearable apparatus 1. In other words, the controller 21 is a control circuit. The controller 21 includes at least one processor for providing control and processing capability to implement various functions as will be described in further detail below.

In accordance with various embodiments, the at least one processor may be implemented as a single integrated circuit (IC) or as multiple communicatively coupled ICs and/or discrete circuits. The at least one processor can be implemented in accordance with various known technologies.

In one embodiment, the processor includes, for example, one or more circuits or units configured to perform one or more data computing procedures or processes by executing instructions stored in an associated memory. In the other embodiments, the processor may be implemented as firmware (e.g. discrete logic components) configured to perform the one or more data computing procedures or processes.

In accordance with the various embodiments, the processor may include one or more processors, controllers, microprocessors, microcontrollers, application specific integrated circuits (ASICs), digital signal processors, programmable logic devices, field programmable gate arrays, any combination of these devices or structures, or combinations of the other known devices and structures to implement the functions described herein.

The controller 21 in this example is one type of arithmetic processing unit and one type of electric circuit. The controller 21 comprises, for example, a central processing unit (CPU) 211, a digital signal processor (DSP) 212, and a storage medium 213. The controller 21 can manage the overall operations of the wearable apparatus 1 by controlling the other constituent elements of the wearable apparatus 1. The controller 21 may further include a co-processor such as a system-on-a-chip (SoC), a micro-control unit (MCU), or a field-programmable gate array (FPGA). The controller 21 may perform various controls through cooperation between the CPU 211 and the co-processor or by switching between the CPU 211 and the co-processor. In other words, the controller 21 is a control circuit.

The storage medium 213 comprises a volatile memory 213a such as a random-access memory (RAM), and a non-volatile memory 213b such as a read-only memory (ROM). The volatile memory 213a and the non-volatile memory 213b are non-transitory recording media that can be read by the CPU 211 and the DSP 212. The non-volatile memory 213b stores a plurality of control programs Pg1 for controlling the wearable apparatuses 1. The various functions of the controller 21 are implemented by causing the CPU 211 and the DSP 212 to execute the various control programs Pg1 in the storage medium 213.

All or part of the functions of the controller 21 may be implemented by a hardware circuit that does not require software for implementing the functions. In other words, the controller 21 may be configured by a circuit. The storage medium 213 may include a non-transitory computer-readable recording medium other than the ROM and the RAM. The storage medium 213 may include, for example, a compact hard disk drive and a solid-state drive (SSD).

Another storage medium may be disposed outside of the controller 21 together with or as a replacement for the storage medium 213. Information to be described later may be stored in the storage medium 213 or the storage medium disposed outside of the controller 21.

The wireless communication unit (communication circuit) 22 is housed in, for example, the main body 2, and comprises an antenna 221. The wireless communication unit 22 can perform wireless communication via the antenna 221 under the control of the controller 21. The wireless communication unit 22 can receive a signal from another wearable apparatus 1 different from the wearable apparatus 1, for example, through a base station or directly via the antenna 221. The wireless communication unit 22 can perform an amplification process and down-conversion on a reception signal and output a resulting signal to the controller 21. The controller 21 can perform, for example, a demodulation process on the reception signal to be input and acquire user data and control data that are included in the reception signal. Furthermore, the wireless communication unit 22 can perform up-conversion and the amplification process on a transmission signal generated by the controller 21, and wirelessly transmit a processed transmission signal via the antenna 221. The other wearable apparatus 1 receives the transmission signal routing the antenna 221, for example, through a base station or directly.

The stimulator 23 can stimulate sense organs in the user's skin by a controllable stimulation quantity with the wearable apparatus 1 worn on the user. The controller 21 controls this stimulator 23. The sense organs in the skin contain a receptor for the sense of touch, the sense of pressure, or the sense of temperature. The stimulator 23 can stimulate these receptors.

FIG. 3 exemplifies that the stimulator 23 comprises the band part 3 and a tightening mechanism 231. The band part 3 is wound around a portion of the body of the user (for example, the arm). The tightening mechanism 231 can tighten the portion of the body of the user (for example, the arm) with a controllable tightening force, using the band part 3. In other words, this stimulator 23 can stimulate the receptors for the sense of pressure in the user's skin by a controllable stimulation quantity.

Figure 4:
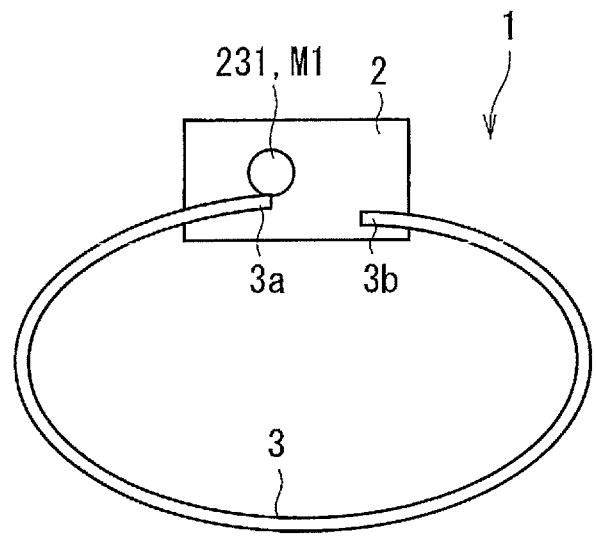
FIG. 4 schematically illustrates one example structure of a wearable apparatus.

FIG. 4 schematically illustrates one example structure of the wearable apparatus 1. FIG. 4 mainly exemplifies the constituent elements of the stimulator 23, and appropriately omits the illustration of the other constituent elements to avoid complication of the illustration. The same holds true for FIGS. 5 to 7 to be referred to later. As exemplified in FIG. 4, the tightening mechanism 231 is housed in, for example, the main body 2. This tightening mechanism 231 may comprise, for example, a motor M1. This motor M1 is rotated under the control of the controller 21. This motor M1 may be any motor, for example, a dynamotor or an AC motor. A predetermined power converter may be disposed, for example, between the battery 27 and the motor M1. Under the control of the controller 21, this power converter converts a voltage from the battery 27 into a desired voltage and outputs this voltage to the motor M. The motor M1 is rotated according to this voltage.

An end 3a of the band part 3 is fixed to the motor M1. The other end 3b of the band part 3 is fixed, for example, inside the main body 2. This band part 3 can be bent and deformed by external forces, mainly to its own normal direction. Thus, rotation of the motor M1 in a predetermined direction (clockwise in FIG. 4) enables the motor M1 to wind a portion of the band part 3. The band part 3 can be formed of a material, for example, an elastic material (e.g., a synthetic resin), fibers (e.g., synthetic fibers), or a metal.

Figure 5:
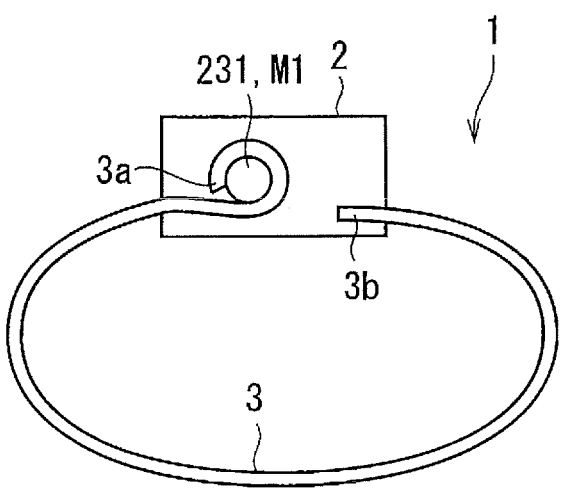
FIG. 5 schematically illustrates one example structure of a wearable apparatus.

FIG. 5 schematically illustrates one example structure of the wearable apparatus 1. FIG. 5 exemplifies that a portion of the band part 3 is wound around the motor M1. In other words, the band part 3 is wound by the motor M1. Thus, the perimeter of the portion of the band part 3 that extends from the main body 2 is shorter than that of the wearable apparatus 1 in FIG. 4. In other words, the motor M1 winds the portion of the band part 3, so that the band part 3 can tighten the arm of the user. The controller 21 can control the tightening force by controlling, for example, output torque of the motor M1.

Conversely, rotation of the motor M1 in a direction opposite to the predetermined direction increases the perimeter of the portion of the band part 3 that extends from the main body 2. Consequently, the motor M1 can loosen the tightening of the arm by the band part 3.

This stimulator 23 can stimulate, for example, the receptors for the sense of pressure in the user's skin of the arm by tightening and loosening the band part 3. In other words, the user can perceive the tightness of the band part 3.

Although the tightening mechanism 231 controls the tightening by the band part 3 by changing the perimeter of the band part 3 that extends from the main body 2 in the example above, the control is not necessarily limited to this. For example, the band part 3 is formed to allow change in its thickness, and the tightening mechanism 231 changes this thickness, which may control the tightening by the band part 3.

Figure 6:
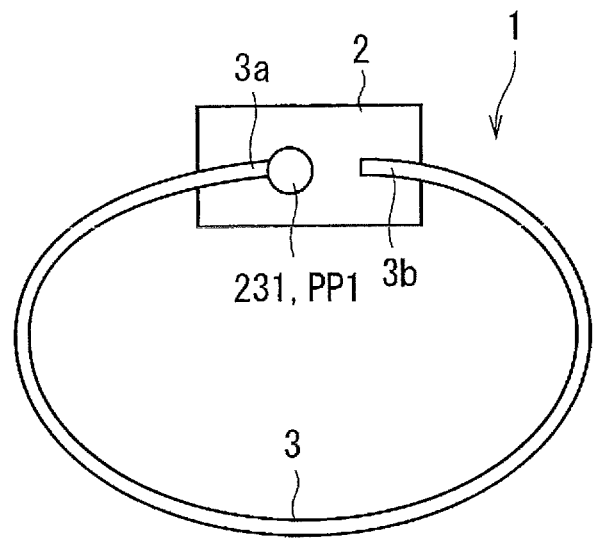
FIG. 6 schematically illustrates one example structure of a wearable apparatus.

FIG. 6 schematically illustrates another example structure of the wearable apparatus 1. FIG. 6 exemplifies that the tightening mechanism 231 comprises, for example, a pump PP1. The controller 21 controls the pump PP1. The band part 3 is formed to allow expansion in its thickness. The band part 3 is formed of a material, for example, a synthetic resin (e.g., a polyethylene resin), an elastic material (e.g., rubber), or fibers (e.g., synthetic fibers), and has an internal space in communication with the pump PP1. This internal space is, for example, opened only at a junction with the pump PP1. In other words, the internal space is shaped like an opened bag in the pump PP1. The pump PP1 can send air from the outside to the internal space or discharge air in the internal space outside.

Figure 7:
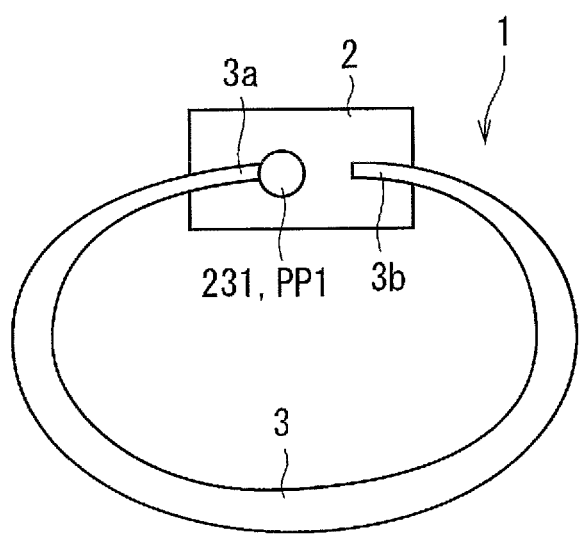
FIG. 7 schematically illustrates one example structure of a wearable apparatus.

The band part 3 expands at least to the inner peripheral side with the air sent to this internal space by the pump PP1. The band part 3 may expand both to the inner peripheral side and the outer peripheral side. FIG. 7 schematically illustrates yet another example structure of the wearable apparatus 1 with the band part 3 expanded. Since the band part 3 expands to the inner peripheral side, the space enclosed by the band part 3 is narrowed. In other words, the pump PP1 can tighten the arm of the user using the band part 3. The controller 21 can control the tightening force by controlling the air flow rate with the pump PP1. On the other hand, the pump PP1 takes in the air in the internal space, resulting in contraction of the band part 3 in the thickness direction. Consequently, the space enclosed by the band part 3 is enlarged. In other words, the pump PP1 can loosen the tightening of the arm of the user by the band part 3.

Expansion and contraction of a component on the inner peripheral side of the band part 3 will suffice for the tightening by the band part 3. In other words, the component on the inner peripheral side of the band part 3 may be formed of a material, for example, a synthetic resin such as a polyethylene resin, an elastic material (e.g., rubber), or fibers (e.g., synthetic fibers).

In the aforementioned example, the thickness of the band part 3 is controlled using, but not necessarily limited to, air as fluid. The thickness of the band part 3 may be controlled, for example, mechanically. One specific example thereof may be application of an apparatus that transforms rotation into thickness like a generally-called z-axis stage. This apparatus may be rotated by a motor. The rotation of the motor changes the thickness of the apparatus.

The apparatus is disposed inside the band part 3 so that the thickness of the apparatus extends in the thickness direction of the band part 3. For example, the band part 3 is shaped like a bag, and the apparatus is housed inside the bag. The band part 3 may comprise a plurality of such apparatuses. Here, the plurality of apparatuses may be disposed, for example, along the circumferential direction. Then, the controller 21 controls the motor, so that the thickness of the apparatuses and further the thickness of the band part 3 are controlled. Consequently, the tightening and loosening of the arm of the user can be controlled.

The input unit 24 is disposed in, for example, the main body 2, and can receive an input from the user to the wearable apparatus 1. The input unit 24 may comprise, for example, an operation button. If the user operates the operation button, the input unit 24 outputs, to the controller 21, an electrical signal indicating that the operation button has been operated. The controller 21 can perform a process corresponding to this electrical signal.

Alternatively, the input unit 24 may be a touch panel. Examples of the touch panel include a projected capacitive touch panel. This touch panel can detect an operation to the display area 251 with an operator such as the finger. If the user operates the display area 251 with an operator such as the finger, the touch panel outputs, to the controller 21, an electrical signal corresponding to the operation. Consequently, the controller 21 can identify, based on the electrical signal from the touch panel, the details of the operation performed on the display area 251 and perform processes corresponding to the details. The user may give various instructions to the wearable apparatus 1 also by operating the display area 251 with an operator other than the finger, such as pens for electrostatic touch panels including a stylus pen.

Alternatively, the wearable apparatus 1 may have a voice input function. Here, the input unit 24 comprises a voice input unit (for example, a microphone), and the controller 21 has a voice recognition function. This input unit 24 can convert the voice input from outside into a sound signal and output the sound signal to the controller 21. The controller 21 recognizes a word based on the input sound signal with the voice recognition function. If the word coincides with a pre-registered word, the controller 21 executes a process corresponding to the word. Consequently, the user can enter the various instructions to the wearable apparatus 1 by voice.

In accordance with various embodiments, the input unit 24 may be implemented using any input technology or any input device that is known in this field, for example, a QWERTY keyboard, a pointing device (e.g., a mouse), a joystick, a stylus, a touch screen display panel, a keypad, one or more buttons, any input technology or any input device that is technically known, or any combinations of these technologies.

The display 25 is housed in, for example, the main body 2. Under the control of the controller 21, this display 25 can display various information on the display area 251. The display 25 may be, for example, a liquid crystal display panel or an organic electro luminescent (EL) panel.

The sensor 26 is disposed in, for example, the main body 2 or the band part 3. The sensor 26 can detect a predetermined physical quantity and output, to the controller 21, a result of the detection. The sensor 26 is, for example, a force sensor. This force sensor may be, for example, a contact-type force sensor, and comprise a force sensitive resistor. The resistance value of this force sensitive resistor is changed according to the force applied to the force sensitive resistor. Thus, the controller 21 can detect the force applied to the sensor 26, based on the voltage and the current of the force sensitive resistor. In other words, the sensor 26 converts the force applied thereto into an electrical signal, and outputs the electrical signal to the controller 21. The controller 21 can recognize the force applied to the sensor 26, based on the electrical signal.

The battery 27 is housed in, for example, the main body 2, and can output the power of the wearable apparatus 1. The power output from the battery 27 is supplied to the various constituent elements, such as the controller 21 and the wireless communication unit 22 included in the wearable apparatus 1.

Figure 8:
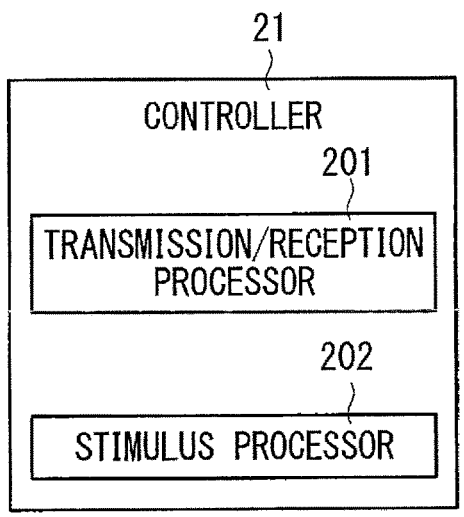
FIG. 8 illustrates a functional block diagram schematically showing one example internal configuration of a controller.

FIG. 8 illustrates a functional block diagram schematically showing one example internal configuration of the controller 21. The controller 21 comprises a transmission/reception processor 201 and a stimulus processor 202. The transmission/reception processor 201 can transmit, to the other wearable apparatus 1 through the wireless communication unit 22, information based on the physical quantity detected by the sensor 26 (to be described later). The information based on the physical quantity will be also referred to as physical information hereinafter. The transmission/reception processor 201 can receive the physical information from the other wearable apparatus 1. The physical information may be, for example, information indicating a physical quantity per se. In other words, the physical information may be a value detected by the sensor 26. The other examples of the physical information will be described later.

Figure 9:
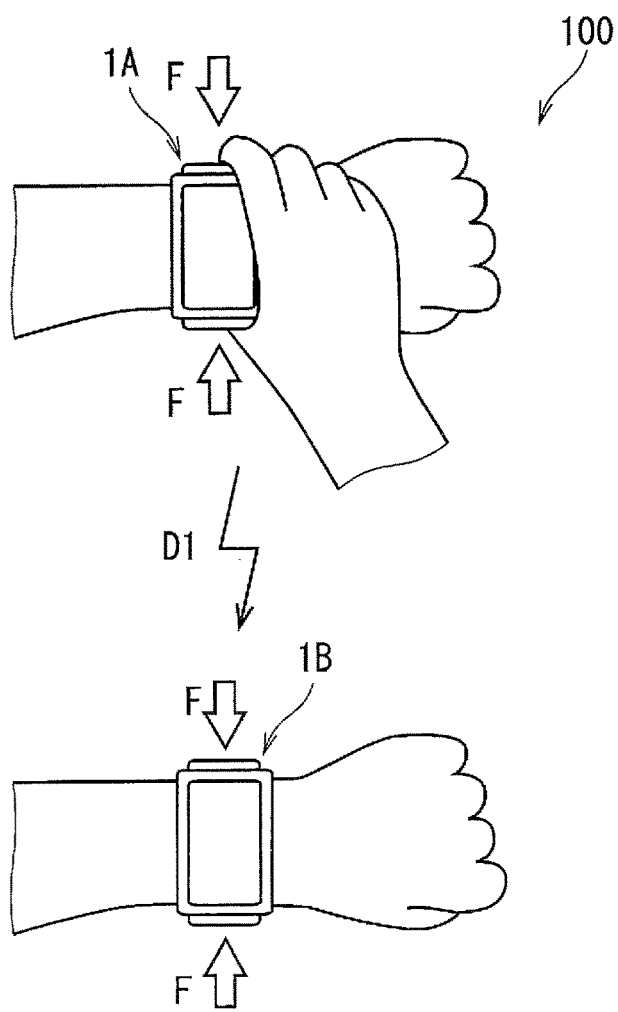
FIG. 9 schematically illustrates one example structure of a wearable apparatus system.

The stimulus processor 202 causes the stimulator 23 to stimulate the sense organs in the user's skin based on the received physical information so that the physical quantity is reproduced on the sense organs in the user's skin. One specific example will be hereinafter described with reference to FIG. 9. FIG. 9 schematically illustrates one example of the wearable apparatus system 100. The constituent elements belonging to the wearable apparatus 1A may append "A" to the reference numerals. The constituent elements belonging to the wearable apparatus 1B may append "B" to the reference numerals. For example, a controller 21A denotes the controller 21 for the wearable apparatus 1A, and a stimulator 23B denotes the stimulator 23 for the wearable apparatus 1B.

As illustrated in FIG. 9, for example, the user UA holds and grasps the wearable apparatus 1A with the hand not wearing the wearable apparatus 1A. Consequently, force F is applied to a sensor 26A. The sensor 26A detects this force F and outputs, to the controller 21, a result of the detection. A transmission/reception processor 201A transmits, for example, physical information D1 indicating the value detected by the sensor 26A to the wearable apparatus 1B through a wireless communication unit 22A.

A transmission/reception processor 201B of the wearable apparatus 1B receives the physical information D1 through a wireless communication unit 22B. A stimulus processor 202B controls a tightening mechanism 231B based on the physical information D1. Specifically, the stimulus processor 202B causes the tightening mechanism 231B to tighten a portion of the body of the user UB (for example, the arm) using a band part 3B so that the force F detected by the sensor 26A should be reproduced by the tightening force.

The stimulus processor 202B may control the motor M1 by generally-called feed-forward control. For example, a relationship between force and voltage values is prestored in the storage medium 213. The stimulus processor 202B may determine a voltage value corresponding to the force F based on the relationship, and apply the voltage value to a motor M1B. Alternatively, the stimulus processor 202B may control the motor M1B by feedback control. Here, the stimulus processor 202B may, for example, calculate a deviation between the force detected by the sensor 26B and the force F and control the motor M1B based on the deviation so that the deviation approximates to zero. Consequently, the wearable apparatus 1B can reproduce the force F more accurately.

In this example, the control for reproducing a physical quantity may be regarded as the control over the stimulator 23 using the physical quantity as a target value (or a command value).

As described above, when the user UA grasps the arm, the arm of the user UB is tightened by the tightening force corresponding to the force F. Consequently, the user UB can vicariously sense the grasping of the arm by the user UA. For example, if the user UA is a parent and the user UB is the child, the parent can gently grasp his/her own arm as if it was the arm of the child. On the other hand, the child can vicariously sense the grasping of the arm by the parent. Consequently, the child can feel secure.

The transmission/reception processor 201A may transmit the physical information only if the physical quantity detected by the sensor 26A is larger than a predetermined reference value. In other words, if the physical quantity is too small, the transmission/reception processor 201A need not transmit the physical information to the wearable apparatus 1B. Even when the physical quantity slightly increases due to noise, etc., the physical information is not transmitted. Thus, unnecessary transmission can be reduced.

Figure 10:
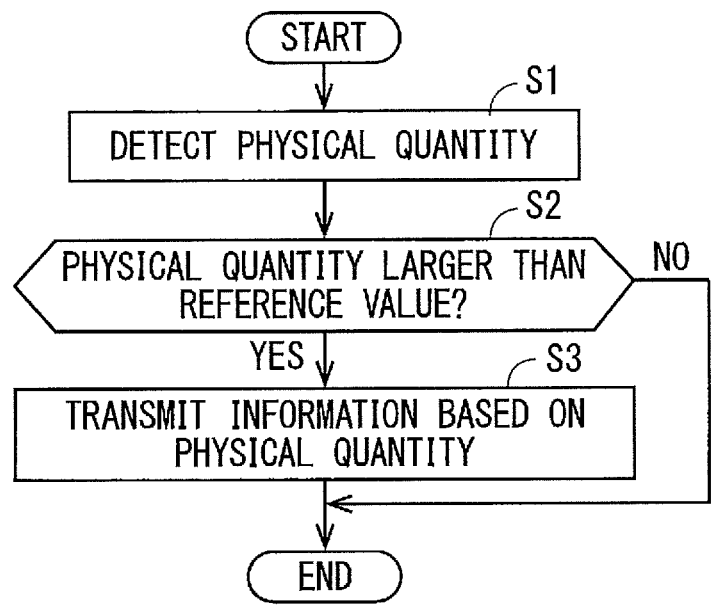
FIG. 10 illustrates a flowchart showing one example of operations of a wearable apparatus.
Figure 11:
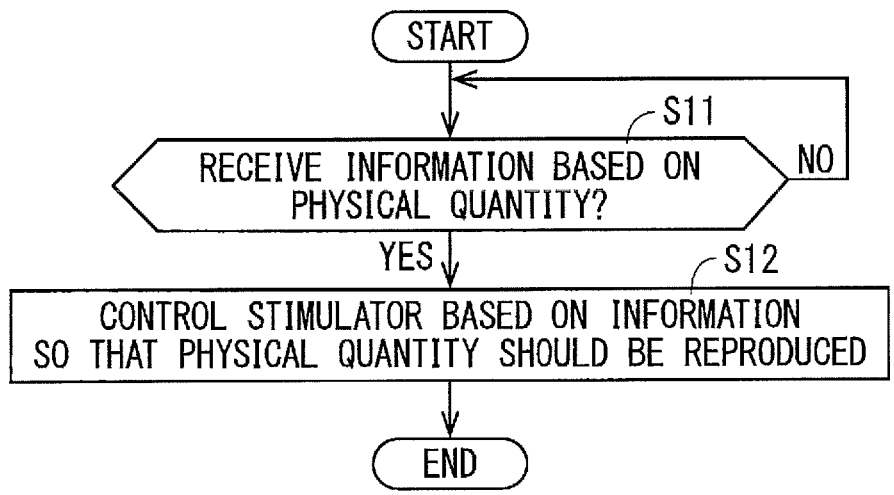
FIG. 11 illustrates a flowchart showing one example of operations of a wearable apparatus.

FIGS. 10 and 11 illustrate flowcharts showing examples of operations of the wearable apparatuses 1A and 1B, respectively. A series of the operations in each of FIGS. 10 and 11 may be repeated, for example, at predetermined time intervals. With reference to FIG. 10, the sensor 26A detects the physical quantity (for example, the force F), and outputs a result of the detection to the controller 21A in Step S1. Next in Step S2, the transmission/reception processor 201A determines whether the physical quantity detected by the sensor 26A is larger than a reference value. This reference value may be predetermined and stored in a storage medium, for example, a positive value close to zero. If determining that the physical quantity is larger than the reference value, the transmission/reception processor 201A transmits information based on the physical quantity (physical information) to the wearable apparatus 1B through the wireless communication unit 22A in Step S3. On the other hand, if determining that the physical quantity is smaller than the reference value in Step S2, the controller 21A ends the processes.

Step S2 is not always necessary. The transmission/reception processor 201 may transmit the physical information based on the physical quantity without any determination in Step S2. This holds true in the other flowcharts to be described later.

With reference to FIG. 11, the transmission/reception processor 201B of the wearable apparatus 1B determines whether to have received the information based on the physical quantity (physical information) through the wireless communication unit 22B in Step S11. If determining no reception of the physical information, the transmission/reception processor 201B executes Step S11 again. If determining the reception of the physical information, the stimulus processor 202B causes the stimulator 23B to stimulate the sense organs in the user's skin of the user UB based on the physical information so that the physical quantity is reduced on the sense organs of the user UB in Step S12. For example, the stimulus processor 202B controls the motor M1B based on the physical information, and tightens the arm of the user UB using the band part 3B as described above.

Although the wearable apparatus 1A transmits the physical information to the wearable apparatus 1B in the aforementioned example, conversely, the wearable apparatus 1B may transmit the physical information to the wearable apparatus 1A. In other words, the wearable apparatus 1B may transmit, to the wearable apparatus 1A, information based on the physical quantity detected by the sensor 26B. Then, the wearable apparatus 1A may tighten the arm of the user UA based on the physical information. Consequently, the user UB can grasp his/her own arm as if it was the arm of the user UA. The user UA can vicariously sense the grasping by the user UB. In other words, the wearable apparatus 1B may perform the operations in FIG. 10, and the wearable apparatus 1A may perform the operations in FIG. 11. This holds true in the other flowcharts to be described later.

With these wearable apparatuses 1, the grasping of the arm by a user can be used as a cue between the users. For example, the grasping once can be used as a greeting cue such as "hello". Consequently, the users UA and UB can communicate with each other using the wearable apparatuses 1. Such communication is particularly effective if the users UA and UB are, for example, under water because no conversation is required between the users UA and UB. The communication using the wearable apparatuses 1 hardly reveals, to the others, the details the user desires to convey. Thus, the user can convey the intention to a particular user while concealing it from the others in a group. The communication using the wearable apparatuses 1 does not require visual recognition between the users UA and UB, unlike the communication using, for example, gesture (e.g., sign language). Thus, the users UA and UB can communicate with each other even when they cannot visually recognize each other.

The cue may be represented by, for example, a grasping pattern. This pattern is represented by, for example, at least one of the number of grasping times, the time during which the grasping is maintained, time intervals for grasping, and the grasping power.

When the wearable apparatus 1A collides with an object and receives an impact from it, the wearable apparatus 1B causes the sense organs in the skin of the user UB to reproduce the force of the impact according the aforementioned control. Thus, the user UB can also vicariously sense the impact between the arm of the user UA and the object.

[Information based on Physical Quantity]

In the aforementioned examples, information indicating a value of the physical quantity detected by the sensor 26 is adopted as a specific example of the physical information based on the physical quantity. If the tightening mechanism 231 comprises, for example, the motor M1, the wearable apparatus 1 may adopt, as the physical information based on the physical quantity, for example, a voltage value to be applied to the motor M1 to reproduce the physical quantity detected by the sensor 26. Furthermore, the stimulus processor 202 may control the motor M1 based on the received voltage value. In other words, the wearable apparatus 1 may transmit information necessary for controlling the stimulator 23 to reproduce the physical quantity, as the physical information based on the physical quantity.

[Aspect of Transmitting Physical Information based on Physical Quantity]

Each time detecting a physical quantity larger than a reference value, the wearable apparatus 1 can transmit the physical information based on the physical quantity with repetition of the operations in FIG. 10. However, the wearable apparatus 1 need not always transmit the physical information on each detection. The wearable apparatus 1 may transmit, for example, the physical information obtained by collecting a plurality of physical quantities (e.g., time-series data on the physical quantities) if detecting the physical quantity a plurality of times. The wearable apparatus 1B may stimulate the sense organs in the user's skin so that the physical quantities is reproduced on the sense organs in the user's skin based on this physical information. Consequently, the number of times the physical information is transmitted can be reduced.

[Designating Transmission Destination]

The wearable apparatus 1 may be able to communicate with the two or more other wearable apparatuses 1. Here, the input unit 24 may receive an input for designating a transmission destination. The storage medium 213 stores, for example, a plurality of pieces of destination information assigned one-to-one to the other wearable apparatuses 1. The input unit 24 may receive an input for designating one of the pieces of destination information. One example of the specific processes will be hereinafter described.

The controller 21 reads the plurality of pieces of destination information from the storage medium 213, and causes the display 25 to display these pieces of information in list form. The controller 21 may display user information (for example, names of the users) of the wearable apparatuses 1 indicated by the plurality of pieces of destination information, as a replacement for or together with the plurality of pieces of destination information. This user information may be, for example, associated with the plurality of pieces of destination information and stored in the storage medium 213. If the user information is displayed, the user easily selects a transmission destination.

While viewing the display area 251 to check the plurality of pieces of destination information, the user designates one of the pieces of destination information using the input unit 24. If the input unit 24 is, for example, a touch panel, the user operates a portion of the display area 251 in which the destination information (or the user information) is displayed, using an operator (for example, the finger). The input unit 24 detects the operation and outputs the information to the controller 21. The controller 21 (the transmission/reception processor 201) sets the operated destination information to a transmission destination based on this information. Then, the transmission/reception processor 201 transmits, to the set transmission destination, the information based on the physical quantity detected by the sensor 26.

[Designating Plurality of Transmission Destinations]

The input unit 24 may receive inputs for designating a plurality of transmission destinations. The controller 21 sets a plurality of pieces of destination information to the transmission destinations in response to the inputs. Then, the transmission/reception processor 201 transmits, to a plurality of the wearable apparatuses 1 that have been set, information based on the physical quantity detected by the sensor 26.

Consequently, for example, when the user grasps the wearable apparatus 1, the arms of a plurality of the other users are tightened by the respective wearable apparatuses 1. Thus, for example, a parent can vicariously grasp the arms of a plurality of children. Conversely speaking, the plurality of children can vicariously sense the grasping by the parent.

Alternatively, the user can give a cue to a plurality of the other users. For example, a certain grasping pattern is determined among a plurality of users (for example, a family) as a cue for gathering at a predetermined meeting place. When one of the users grasps the wearable apparatus 1 in the pattern, the cue can be conveyed to all the other users. Upon receipt of the cue, the users move to the meeting place. Thus, all the users gather.

[Temperature]
[Reproduction of Temperature Change]

Figure 12:
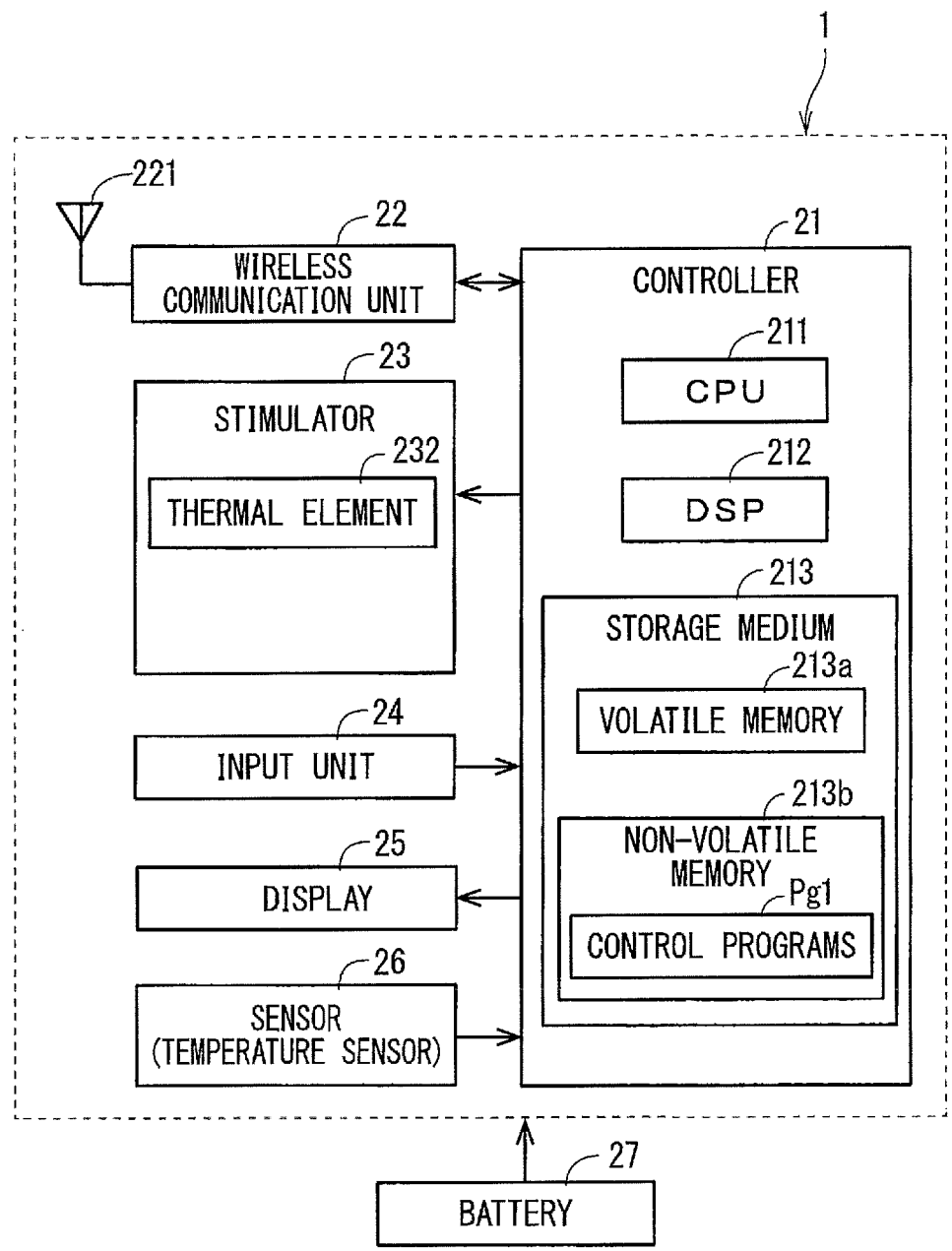
FIG. 12 illustrates a functional block diagram schematically showing one example electrical configuration of a wearable apparatus.

FIG. 12 illustrates a functional block diagram schematically showing one example electrical configuration of the wearable apparatus 1. The wearable apparatus 1 in FIG. 12 differs from that in FIG. 3 in regard to the stimulator 23 and the sensor 26.

FIG. 12 exemplifies that the sensor 26 is, for example, a temperature sensor that detects the temperature as a physical quantity. The temperature sensor may comprise, for example, a temperature resistor for detecting the temperature. The resistance value of this temperature resistor is changed depending on the temperature. Thus, the controller 21 can detect the temperature of the temperature resistor, based on the voltage and the current of the temperature resistor. In other words, the sensor 26 can convert the temperature into an electrical signal and output this electrical signal to the controller 21. Consequently, the controller 21 can recognize the temperature based on this electrical signal.

This sensor 26 is disposed in, for example, the main body 2 or the band part 3 to enable detection of the body temperature of the user. The sensor 26 may directly detect the body temperature in contact with the skin of the user. Alternatively, the sensor 26 may receive heat from the user through the main body 2 or the band part 3. In other words, the sensor 26 may indirectly detect the body temperature of the user.

The transmission/reception processor 201 transmits, to the other wearable apparatus 1 through the wireless communication unit 22, physical information based on the temperature detected by the sensor 26. The transmission/reception processor 201 receives the physical information based on the temperature from the other wearable apparatus 1 through the wireless communication unit 22. The physical information based on the temperature may be, for example, information indicating the temperature per se.

The stimulator 23 may comprise, for example, a thermal element 232. The controller 21 controls the thermal element 232. The thermal element 232 generates or absorbs controllable heat. Consequently, the thermal element 232 can exchange the controllable heat with a worn portion of the user (for example, the arm). In other words, the thermal element 232 can warm or cool the worn portion of the user under the control of the controller 21. In other words, the thermal element 232 can stimulate the receptors for the sense of temperature in the user's skin by a controllable stimulation quantity.

The thermal element 232 is, for example, a heater or a Peltier device. The heater can generate the heat. The Peltier device can generate or absorb the heat. The heater comprises, for example, an electrically heated wire. The stimulus processor 202 controls the current flowing through this electrically heated wire to enable control of the quantity of heat generated by the heater. The magnitude of the current flowing through this electrically heated wire may be controlled by, for example, connecting a direct current (DC)- to-DC converter between the battery 27 and the electrically heated wire and controlling this DC-to-DC converter by the stimulus processor 202. As the current flowing through the electrically heated wire is larger, the quantity of heat is larger.

The Peltier device comprises, for example, first to third metal plates, and first and second semiconductors. The first semiconductor is, for example, a p-type semiconductor, and is connected between the first and second metal plates. The second semiconductor is, for example, an n-type semiconductor, and is connected between the second and third metal plates. In such a Peltier device, upon application of a current from the first metal plate to the third metal plate, the first metal plate discharges heat, and the second metal plate absorbs the heat due to the Peltier effect. Upon application of a current in the reverse direction, the second metal plate discharges heat, and the third metal plate absorbs the heat due to the Peltier effect.

This Peltier device may be disposed, for example, to direct the second metal plate toward the user's arm (i.e., the inner peripheral side of the wearable apparatus 1) and direct the first and third metal plates opposite to the user's arm (i.e., the outer peripheral side). The stimulus processor 202 can generate or absorb heat on the second metal plate side by controlling the direction of the direct voltage between the first and third metal plates. In other words, the Peltier device can give the heat to the user's arm or absorb heat from the user's arm.

The direction of the direct voltage may be controlled by, for example, disposing a switch for switching a connection relationship between the high-potential and low-potential output terminals of the battery 27 and the first and third metal plates and controlling the switch by the stimulus processor 202. The stimulus processor 202 can control the quantity of heat by controlling the magnitude of the direct voltage. The direct voltage may be controlled by, for example, connecting a DC-to-DC converter between the battery 27 and the Peltier device and controlling this DC-to-DC converter by the stimulus processor 202.

The stimulus processor 202 controls the thermal element 232 based on the physical information received from the other wearable apparatus 1 so that the temperature change should be reproduced.

For example, the sensor 26A of the wearable apparatus 1A repeatedly detects the body temperature of the user UA. The transmission/reception processor 201A transmits, for example, information indicating change in the temperatures to the wearable apparatus 1B as the physical information based on the temperatures. The change in the temperatures may be, for example, a change from the normal body temperature of the user. For example, the sensor 26A may detect this normal body temperature. Specifically, the input unit 24A may receive, for example, an input for detecting the normal body temperature. In response to this input, the controller 21A stores the temperature detected by the sensor 26A in the storage medium 213 as the normal body temperature. Then, the controller 21A may calculate a temperature difference between the normal body temperature and a temperature detected with the timing different from that with which the normal body temperature has been detected, and transmit information indicating the temperature difference as information indicating the temperature change.

The transmission/reception processor 201B of the wearable apparatus 1B receives the physical information based on the temperature. Then, the stimulus processor 202B controls the thermal element 232 based on the physical information so that this temperature change should be reproduced on the sense organs in the user's skin. For example, if the temperature is increasing, the stimulus processor 202B causes the thermal element 232B to generate the heat corresponding to the increment.

The stimulus processor 202B may perform, for example, feed-forward control. For example, a relationship between the temperature difference and the current is prestored in the storage medium 213. The stimulus processor 202B may understand the temperature difference of the user UA based on the physical information received from the wearable apparatus 1A, and apply the current determined based on this temperature difference and the aforementioned relationship to the heater or the Peltier device. Alternatively, the stimulus processor 202B may perform, for example, feedback control. For example, the normal body temperature of the user UB is stored in the storage medium 213 of the wearable apparatus 1B. The normal body temperature of this user UB may be stored in the storage medium 213 in a similar manner as that of the normal body temperature of the user UA. The stimulus processor 202B calculates a temperature difference between the temperature detected by the sensor 26B and the normal body temperature of the user UB, and then calculates a deviation between the temperature difference of the user UB and the temperature difference of the user UA. The stimulus processor 202B may control the quantity of heat of the heater or the Peltier device based on the deviation so that this deviation approximates to zero. Consequently, the arm of the user UB can be warmed by the increment of the body temperature of the user UA with higher precision.

Since the arm of the user UB is warmed according to increase in the body temperature of the user UA, the user UB can vicariously sense the increase in the body temperature of the user UA.

If the thermal element 232B is a Peltier device, it can absorb heat from the user. Thus, the wearable apparatus 1B can, for example, reproduce decrease in the body temperature of the user UA. The physical information based on this decrease in the temperature is transmitted from the wearable apparatus 1A to the wearable apparatus 1B. The stimulus processor 202B causes the thermal element 232B to absorb the heat corresponding to the decrement based on this physical information. One example of the specific control is described above. Consequently, the arm of the user UB is cooled according to decrease in the body temperature of the user UA. Thus, the user UB can vicariously sense the decrease in the body temperature of the user UA.

As described above, the user UB can sense change in the body temperature of the user UA. Thus, the user UB can perform a process corresponding to the change in the body temperature of the user UA. For example, if the user UA is a child and the user UB is the parent, the parent can pick up the child and perform an appropriate process.

With the wearable apparatuses 1, the user UB can know information on the change in the body temperature of the user UA not by, for example, numeric characters but can vicariously sense the actual change in the body temperature. Thus, the user UB easily sympathizes with a state of the user UA. Thus, if change in the body temperature suddenly occurs, the user UB actually feels the urgency with ease.

Figure 13:
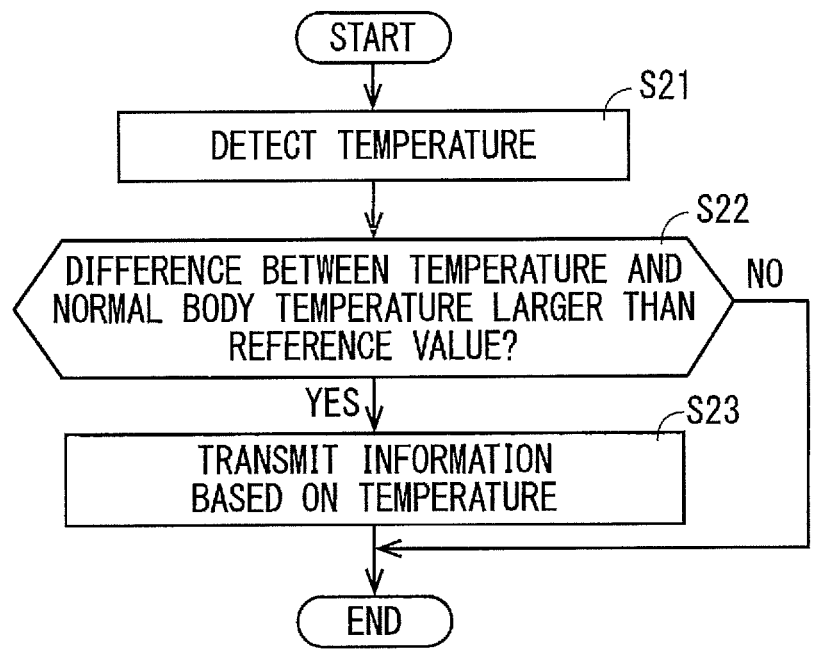
FIG. 13 illustrates a flowchart showing one example of operations of a wearable apparatus.
Figure 14:
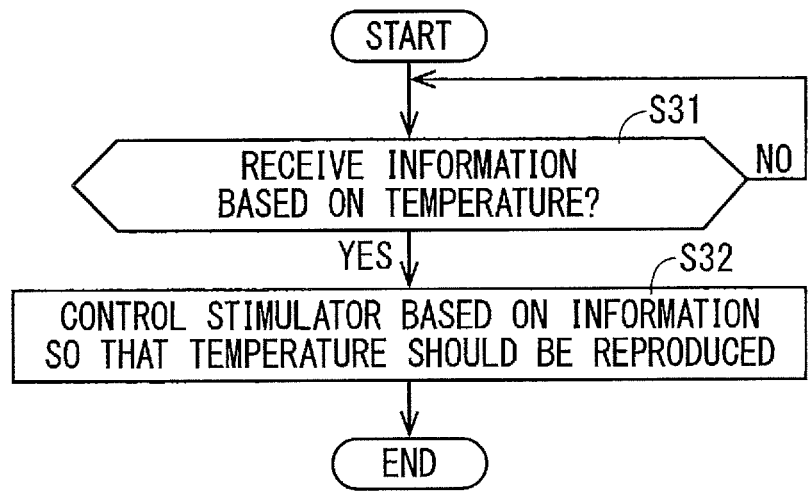
FIG. 14 illustrates a flowchart showing one example of operations of a wearable apparatus.

FIGS. 13 and 14 illustrate flowcharts showing examples of operations of the wearable apparatuses 1A and 1B, respectively. A series of the operations in each of FIGS. 13 and 14 may be repeated, for example, at predetermined time intervals. With reference to FIG. 13, the sensor 26A detects the temperature, and outputs a result of the detection to the controller 21A in Step S21. Next in Step S22, the transmission/reception processor 201A determines whether a temperature difference between the temperature detected by the sensor 26A and the normal body temperature stored in the storage medium 213 is larger than a temperature-difference reference value. This temperature-difference reference value may be predetermined and stored in the storage medium 213, for example, a positive value close to zero. If determining that the temperature difference is larger than the temperature-difference reference value, the transmission/reception processor 201A transmits physical information based on the temperature (for example, information indicating the temperature difference) to the wearable apparatus 1B through the wireless communication unit 22A in Step S23. On the other hand, if determining that the temperature difference is smaller than the temperature-difference reference value in Step S22, the controller 21A ends the processes.

The controller 21 may execute Step S23 without executing Step S22. In Step S22, the physical information based on the temperature is not transmitted even if the temperature increases or decreases by, for example, noise. Thus, unnecessary transmission can be reduced.

With reference to FIG. 14, the transmission/reception processor 201B determines whether to have received the physical information based on the temperature through the wireless communication unit 22B in Step S31. If determining no reception of the physical information, the transmission/reception processor 201B executes Step S31 again. If determining the reception of the physical information, the stimulus processor 202B controls the thermal element 232 based on the physical information so that the temperature change should be reproduced in Step S32.

[Reproduction of Temperature Change]

In the aforementioned example, the wearable apparatus 1B reproduces the temperature change between the temperature detected by the sensor 26A of the wearable apparatus 1A and the normal body temperature. However, the wearable apparatus 1B may reproduce the temperature detected by the sensor 26A per se. In other words, the stimulus processor 202B may cause the thermal element 232B to exchange heat with the worn portion of the user UB so that the temperature detected by the sensor 26A should be reproduced. For example, the stimulus processor 202B may control the thermal element 232B so that the temperature detected by the sensor 26B almost coincides with the temperature detected by the sensor 26A of the wearable apparatus 1A. Consequently, the user UB can vicariously sense the body temperature of the user UA.

[Reproduction of Temperature Distribution]

Figure 15:
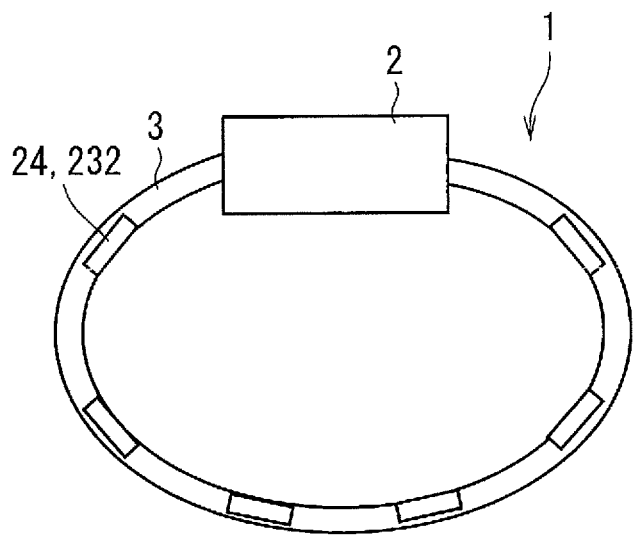
FIG. 15 schematically illustrates one example structure of a wearable apparatus.

FIG. 15 schematically illustrates one example structure of the wearable apparatus 1. As exemplified in FIG. 15, the wearable apparatus 1 may comprise a plurality of the thermal elements 232. These thermal elements 232 may be aligned along, for example, the circumferential direction of the band part 3. For example, the band part 3 may comprise a flexible printed circuit, and the plurality of thermal elements 232 (e.g., electrically heated wires or Peltier devices) may be disposed on this circuit. The controller 21 is separately connected to each of the thermal elements 232 to enable separate control over the quantities of heat of the thermal elements 232.

The wearable apparatus 1 may also comprise a plurality of the sensors 26. These sensors 26 may be aligned along the circumferential direction of the band part 3. The sensors 26 may be disposed on the flexible printed circuit. The plurality of the sensors 26 detect temperatures at a plurality of different positions. In other words, the sensors 26 detect the temperatures at a plurality of positions as physical quantities.

The number of the sensors 26 may be equal to that of the thermal elements 232. Here, the positions of the sensors 26 in the circumferential direction may coincide with the positions of the thermal elements 232 in the circumferential direction. Specifically, part of the positions of the sensors 26 in the circumferential direction may coincide with part of the positions of the thermal elements 232 in the circumferential direction.

The transmission/reception processor 201A may transmit, to the wearable apparatus 1B, physical information based on the temperatures detected by the plurality of sensors 26A. The transmission/reception processor 201B of the wearable apparatus 1B receives this physical information. Then, the stimulus processor 202B may control the plurality of thermal elements 232 based on the physical information so that the temperature distribution of the wearable apparatus 1A should be reproduced on the sense organs in the skin of the user UB.

For example, the stimulus processor 202B separately controls the quantities of heat of the thermal elements 232B so that the temperature detected by each of the sensors 26B approximates to the temperature detected by a corresponding one of the sensors 26A. Consequently, the wearable apparatus 1B reproduces the temperature distribution of the wearable apparatus 1A.

Figure 16:
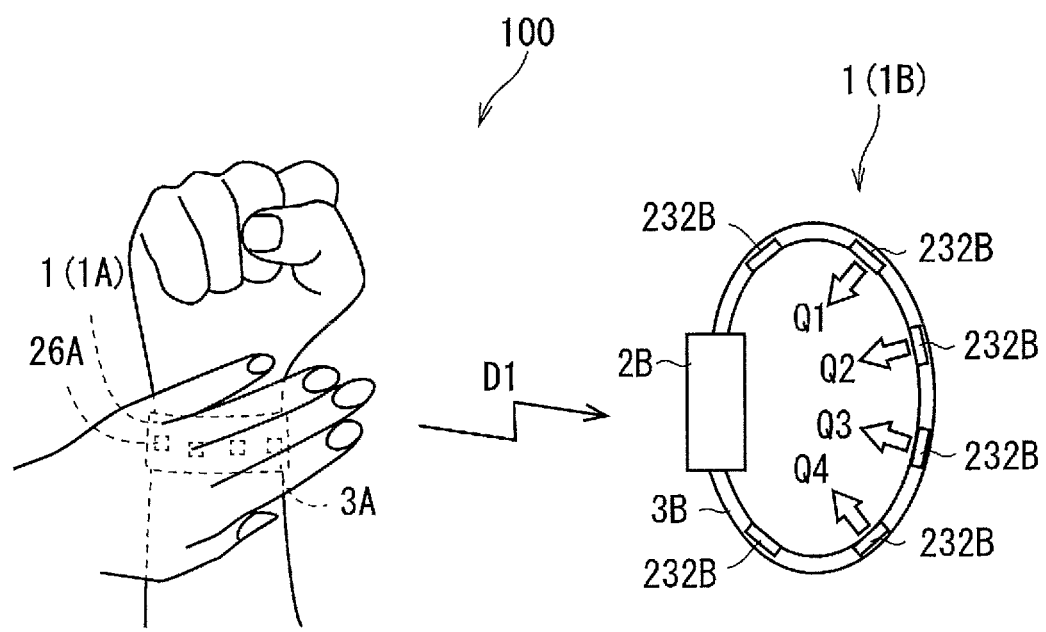
FIG. 16 schematically illustrates one example structure of a wearable apparatus system.

FIG. 16 illustrates one example structure of the wearable apparatus system 100. As illustrated in FIG. 16, for example, the user UA warms a portion of the band part 3 by covering the portion of the band part 3 with the palm of the hand not wearing the wearable apparatus 1A. Consequently, detection temperatures of a plurality of sensors 26A disposed in the portion of the band part 3 covered with the hand increase. Since four of the sensors 26A are covered with the palm of the hand in the wearable apparatus 1 exemplified in FIG. 16, the temperatures detected by these four sensors 26A increase. Assume herein, as one example, that six of the sensors 26A are aligned along the circumferential direction and among the six sensors 26A, the four sensors 26A except for the sensors 26A at both ends are covered with the palm of the hand.

The transmission/reception processor 201A of the wearable apparatus 1A transmits, to the wearable apparatus 1B, physical information D1 based on the temperatures detected by all the sensors 26A. The physical information D1 contains, for example, the detection temperatures obtained by all the sensors 26A. The transmission/reception processor 201B of the wearable apparatus 1B receives the physical information D1. The stimulus processor 202B separately controls the plurality of thermal elements 232 based on this physical information D1. FIG. 16 exemplifies six of the thermal elements 232 as many as the sensors 26. The stimulus processor 202B separately controls the thermal elements 232B disposed in positions corresponding to the sensors 26A, based on the physical information D1.

The stimulus processor 202B may control the thermal elements 232B so that the temperature detected by each of the sensors 26B approximates to the temperature detected by a corresponding one of the sensors 26A as one specific example. In other words, the stimulus processor 202B may control one of the thermal elements 232B based on the temperature detected by a corresponding one of the sensors 26A. Consequently, the thermal elements 232B can be controlled by a simple control method.

The stimulus processor 202B may perform feed-forward control or feedback control. The stimulus processor 202B may, for example, apply the current corresponding to the temperature detected by each of the sensors 26A to a corresponding one of the thermal elements 232B (feed-forward control). Alternatively, the stimulus processor 202B may calculate a deviation between the temperature detected by each of the sensors 26A and the temperature detected by a corresponding one of the sensors 26B, and control a corresponding one of the thermal elements 232B based on this deviation so that the deviation approximates to zero (feedback control).

Since detection temperatures of the four sensors 26A except for the sensors 26A at both ends increase, four of the thermal elements 232B except for the thermal elements 232B at both ends mainly generate the respective quantities of heat Q1 to Q4.

When the user UA warms a portion of the band part 3A in the wearable apparatus 1 by covering it with the palm of the hand, a corresponding portion of the band part 3B of the user UB (a portion corresponding to the portion of the band part 3A) is warmed. Thus, the user UB can sense the warming at the same portion as that of the user UA. Thus, for example, if the user UA is a parent and the user UB is the child, the parent can vicariously warm the arm of the child with the palm of the hand. Conversely, the child can vicariously sense the warming as if his/her own arm was warmed by the palm of the hand of the parent. Consequently, the parent can make the child feel secure.

[Reproduction of Force and Temperature]

The sensor 26 may comprise a force sensor and a temperature sensor. The transmission/reception processor 201A of the wearable apparatus 1A may transmit, to the wearable apparatus 1B, physical information based on the force and the temperature detected by these sensors. Furthermore, the stimulus processor 202B may control the stimulator 23 based on the received physical quantities so that the force and the temperature should be reproduced. Consequently, for example, when the user UA grasps the wearable apparatus 1A, the user UB can sense not only the force obtained by the grasping of the user UA but also increase in the temperature by the grasping. Thus, if the user UA is a parent and the user UB is the child, the parent can make the child feel more secure.

[Physical Quantity]

In a plurality of the examples above, the physical quantity is a physical quantity perceivable by the sense organs in the skin, such as the force or the temperature. The wearable apparatus 1 stimulates the sense organs identical to the sense organs that can perceive the physical quantity, based on the received physical information. Thus, the user can sense the physical quantity through the sense organs of the same type. Thus, the user can actually sense the states of the other users.

[Biological Information]

Figure 17:
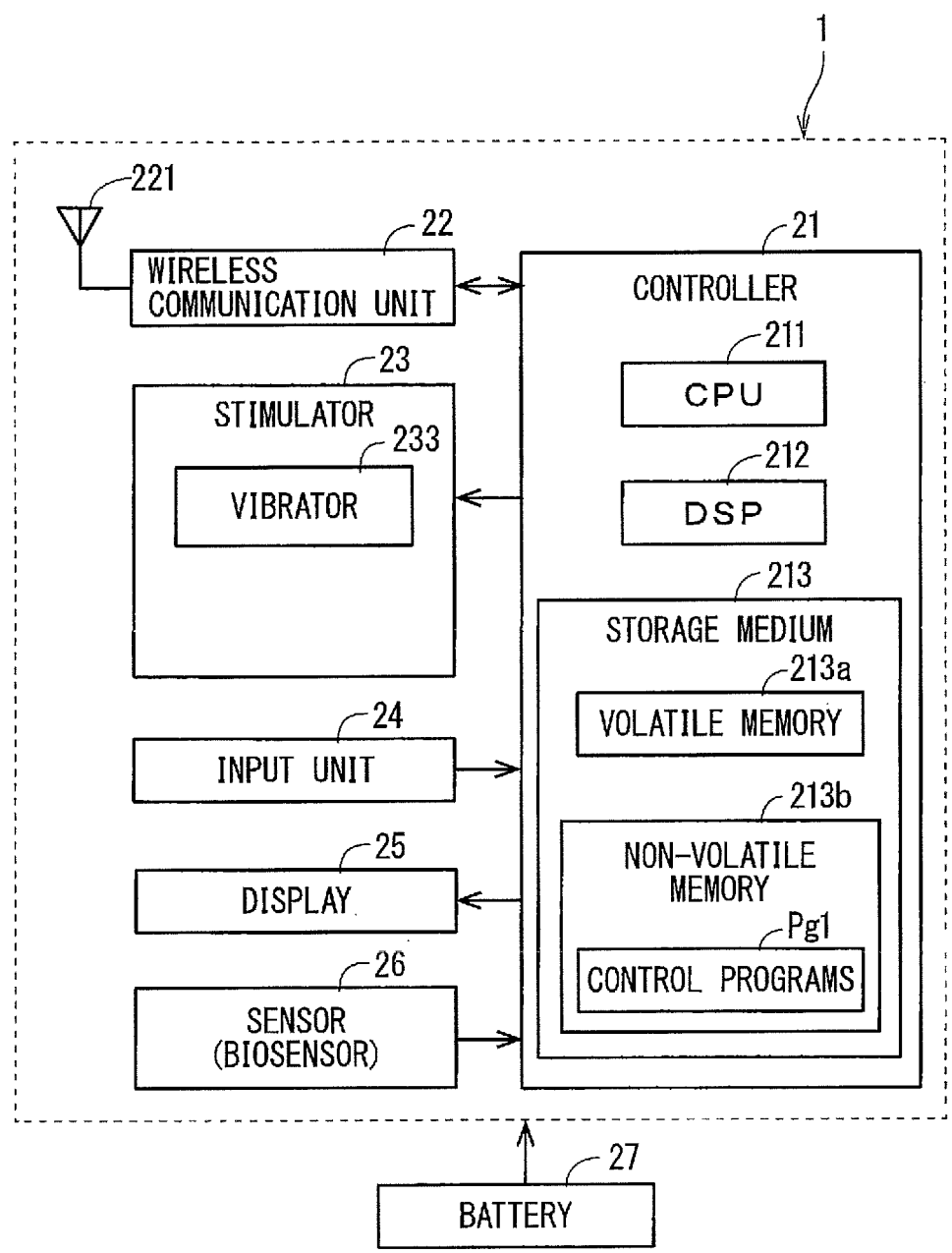
FIG. 17 illustrates a functional block diagram schematically showing one example electrical configuration of a wearable apparatus.
Figure 18:
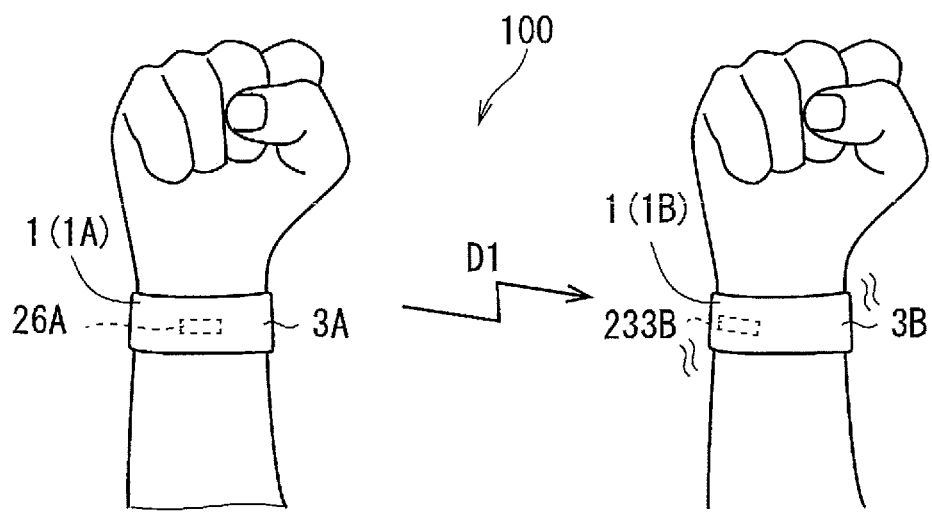
FIG. 18 schematically illustrates one example structure of a wearable apparatus system.

FIG. 17 illustrates a functional block diagram schematically showing one example electrical configuration of the wearable apparatus 1. FIG. 18 schematically illustrates one example structure of a wearable apparatus system. The wearable apparatus 1 in FIG. 17 differs from that in FIG. 3 in regard to the stimulator 23 and the sensor 26.

The sensor 26 may be, for example, a biosensor that detects biological information that periodically varies. The sensor 26 is, for example, a heart rate sensor. The heart rate sensor can detect the rhythm of the heart rate of the user. The heart rate sensor comprises, for example, a light source and photodetectors. The light source emits light to the skin of the user, and the photodetectors receive the reflected light. Since the reflected light varies according to change in the bloodstream, the heart rate sensor can obtain the rhythm of the heart rate based on variation in the reflected light. This rhythm of heart rate can be represented by, for example, time-series data on blood flow (or blood pressure) of blood per small time which passes through a blood vessel per unit area.

The sensor 26 may be disposed at, for example, a position corresponding to an artery in the wrist. This is because the artery in the wrist eases detection of the rhythm of the heart rate. FIG. 18 exemplifies that the sensor 26A is disposed in the band part 3 at a position corresponding to an artery in the wrist of the user UA.

The transmission/reception processor 201 transmits, to the other wearable apparatus 1, the physical information D1 based on this rhythm of heart rate. For example, the time-series data on blood flow may be adopted as the physical information D1 based on this rhythm of heart rate. In other words, the controller 21 generates the physical information D1 indicating the time-series data on blood flow, based on a result of the detection by the sensor 26, and transmits this to the other wearable apparatus 1. Conversely, the transmission/reception processor 201 receives, from the other wearable apparatus 1, the physical information D1 based on this rhythm of heart rate.

The stimulator 23 may comprise, for example, a vibrator 233. This vibrator 233 vibrates under the control of the controller 21. This vibration is conveyed to the user through, for example, the main body 2 or the band part 3. The vibrator 233 may comprise, for example, an eccentric motor. The controller 21 can cause this eccentric motor to rotate to generate vibrations. The vibrator 233 can, for example, stimulate the receptors for the sense of pressure in the user's skin.

The stimulus processor 202 causes the vibrator 233 to vibrate based on the physical information so that, for example, the rhythm of heart rate should be reproduced on the sense organs in the user's skin. The stimulus processor 202, for example, detects a period of change in the blood flow based on the physical information. The stimulus processor 202 may detect the period based on the timing with which the blood flow takes a peak value or a bottom value. Then, the stimulus processor 202 causes the vibrator 233 to vibrate with the period. The stimulus processor 202 causes the vibrator 233 to vibrate, for example, with the timing over a shorter period of time (a duration shorter than the period). Consequently, the vibrator 233 can vibrate at the rhythm of heart rate. FIG. 18 schematically exemplifies the vibrations of the wearable apparatus 1B using four wave lines Since the vibrator 233B vibrates at the rhythm of heart rate, the user UB can vicariously sense the rhythm of heart rate of the user UA. Thus, the user UB more easily feels the urgency when the heart rate of the user UA increases than, for example, when the heart rate is notified merely by numeric characters.

Alternatively, if the user UA is a parent and the user UB is the child, the child can vicariously sense the rhythm of heart rate of the parent. For example, if the child stays home alone and is able to sense the heart rate of the parent, the parent can make the child feel secure.

Figure 19:
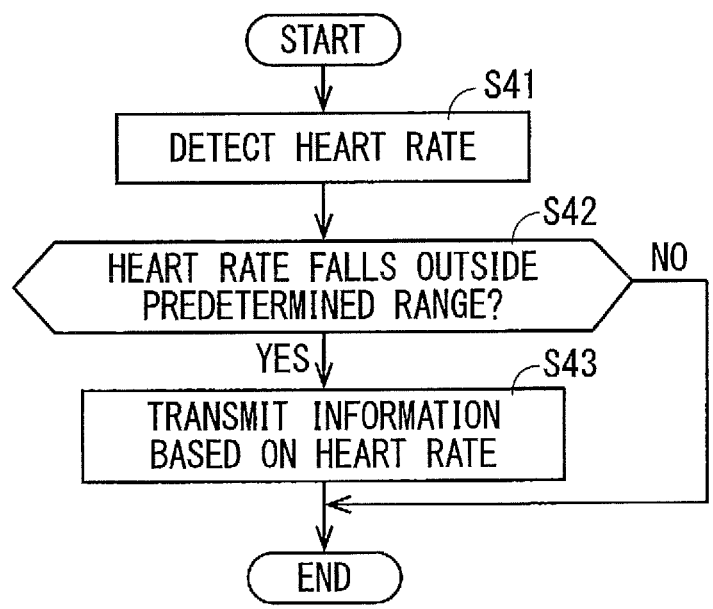
FIG. 19 illustrates a flowchart showing one example of operations of a wearable apparatus.
Figure 20:
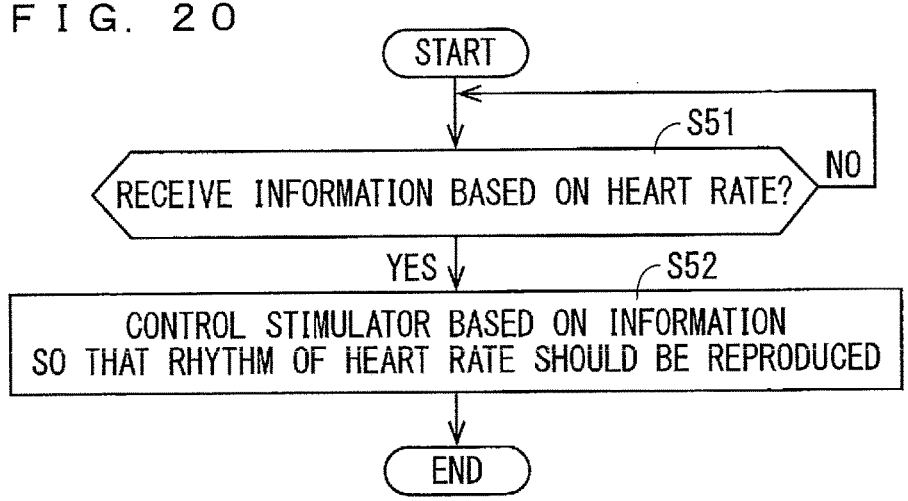
FIG. 20 illustrates a flowchart showing one example of operations of a wearable apparatus.

FIGS. 19 and 20 illustrate flowcharts showing examples of operations of the wearable apparatuses 1A and 1B, respectively. A series of the operations in each of FIGS. 19 and 20 may be repeated, for example, at predetermined time intervals. With reference to FIG. 19, the sensor 26A detects the heart rate, and outputs a result of the detection to the controller 21A in Step S41. Next in Step S42, the transmission/reception processor 201A determines whether this heart rate falls outside a predetermined range. The predetermined range may be predetermined and stored in the storage medium 213. If determining that the heart rate falls outside the predetermined range, the transmission/reception processor 201A transmits physical information based on the heart rate (for example, the time-series data on the blood flow) to the wearable apparatus 1B through the wireless communication unit 22A in Step S43. On the other hand, if determining that the heart rate falls within the predetermined range in Step S42, the controller 21A ends the processes.

The controller 21 may execute Step S43 without executing Step S42. If the heart rate detected by the sensor 26A falls within the predetermined range in Step S42, the physical information is not transmitted. Thus, the physical information based on the heart rate is not transmitted even when the heart rate increases or decreases by, for example, noise. Consequently, unnecessary transmission can be reduced.

With reference to FIG. 20, the transmission/reception processor 201B determines whether to have received the physical information based on the heart rate through the wireless communication unit 22B in Step S51. If determining no reception of the physical information, the transmission/reception processor 201B executes Step S51 again. If determining the reception of the physical information, the stimulus processor 202B causes the vibrator 233 to vibrate as described above so that the rhythm of heart rate should be reproduced on the sense organs in the user's skin of the user UB in Step S52.

The stimulus processor 202 may reproduce the rhythm of heart rate not necessarily by the vibrations but by, for example, the tightening of the arm of the user. The stimulus processor 202 may tighten the arm of the user over a short period of time with the timing, using the band part 3.

The physical information is not limited to the time-series data on the blood flow. The transmission/reception processor 201 may transmit, as the physical information based on the rhythm of heart rate, information indicating, for example, the timing with which the blood flow takes the peak value or the period of the blood flow. Then, in the wearable apparatus 1 after receipt of the information, the stimulus processor 202 may cause the stimulator 23 to stimulate the user's skin with the period. In other words, the transmission/reception processor 201 may transmit information necessary for causing the stimulator 23 to stimulate the sense organs in the user's skin at the rhythm of heart rate.

[Transmission Trigger for Physical Information based on Physical Quantity]

The input unit 24A may receive an input for instructing transmission of the physical information. In other words, the transmission/reception processor 201A may use this input as one of transmission conditions on the physical information. Consequently, it is possible to determine whether the user UA transmits the physical information.

Alternatively, the transmission/reception processor 201A may use reception of a transmission request from the wearable apparatus 1B as one of the transmission conditions on the physical information. For example, if the user UB enters an instruction for requesting the physical information to the input unit 24B of the wearable apparatus 1B, the transmission/reception processor 201B transmits a request signal for the physical information to the wearable apparatus 1A. The transmission/reception processor 201A of the wearable apparatus 1A may transmit the physical information to the wearable apparatus 1B, considering reception of this request signal as one of the transmission conditions on the physical information. Consequently, for example, if desiring to sense the heart rate of the user UA, the user UB can sense the heart rate by entering the request instruction to the input unit 24B.

[Acceleration]

The wearable apparatus 1 reproduces the biological information that periodically varies using the sense organs in the user's skin in the aforementioned example. However, the objects to be reproduced are not limited to the biological information. In other words, the wearable apparatus 1 may reproduce the physical quantity that periodically varies. For example, if the user periodically moves the wearable apparatus 1, the rhythm of spatial movement of this wearable apparatus 1 may be reproduced on the sense organs in the skin. The details will be hereinafter described.

Figure 21:
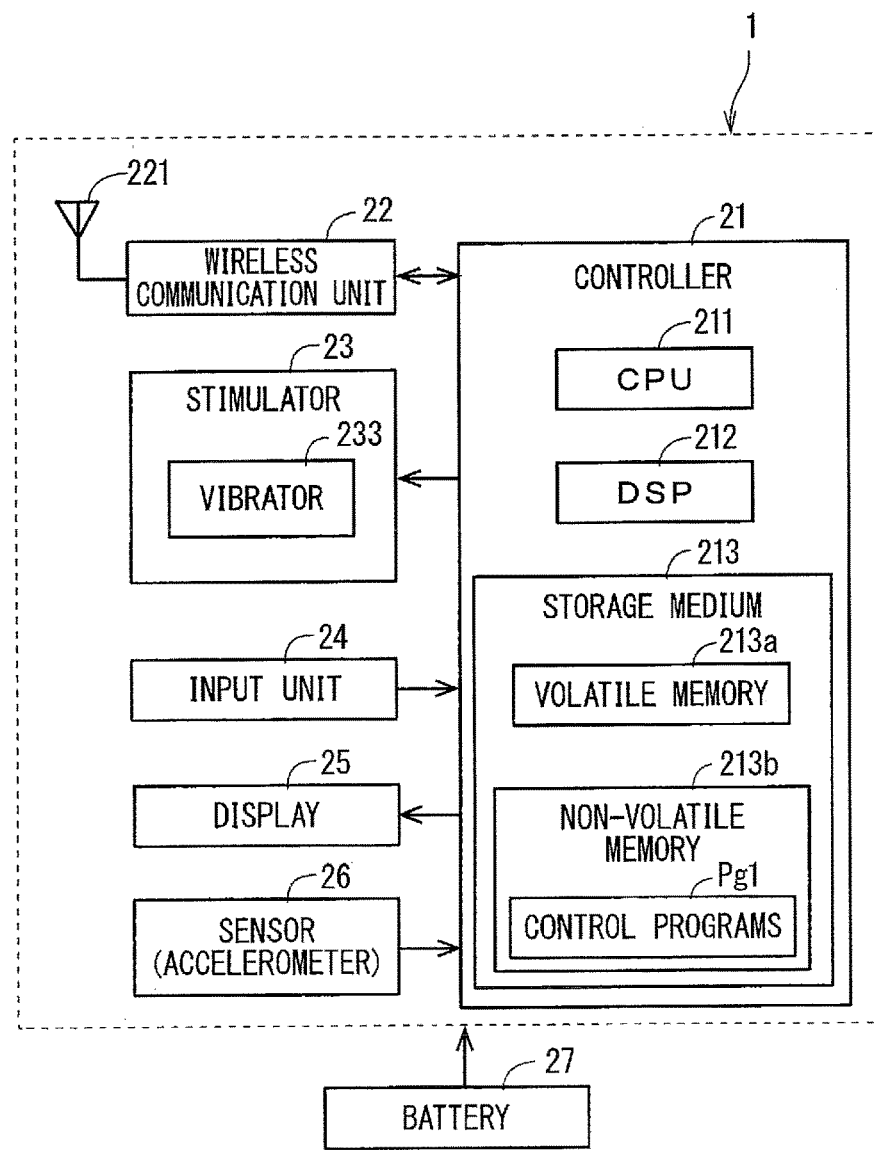
FIG. 21 illustrates a functional block diagram schematically showing one example electrical configuration of a wearable apparatus.
Figure 22:
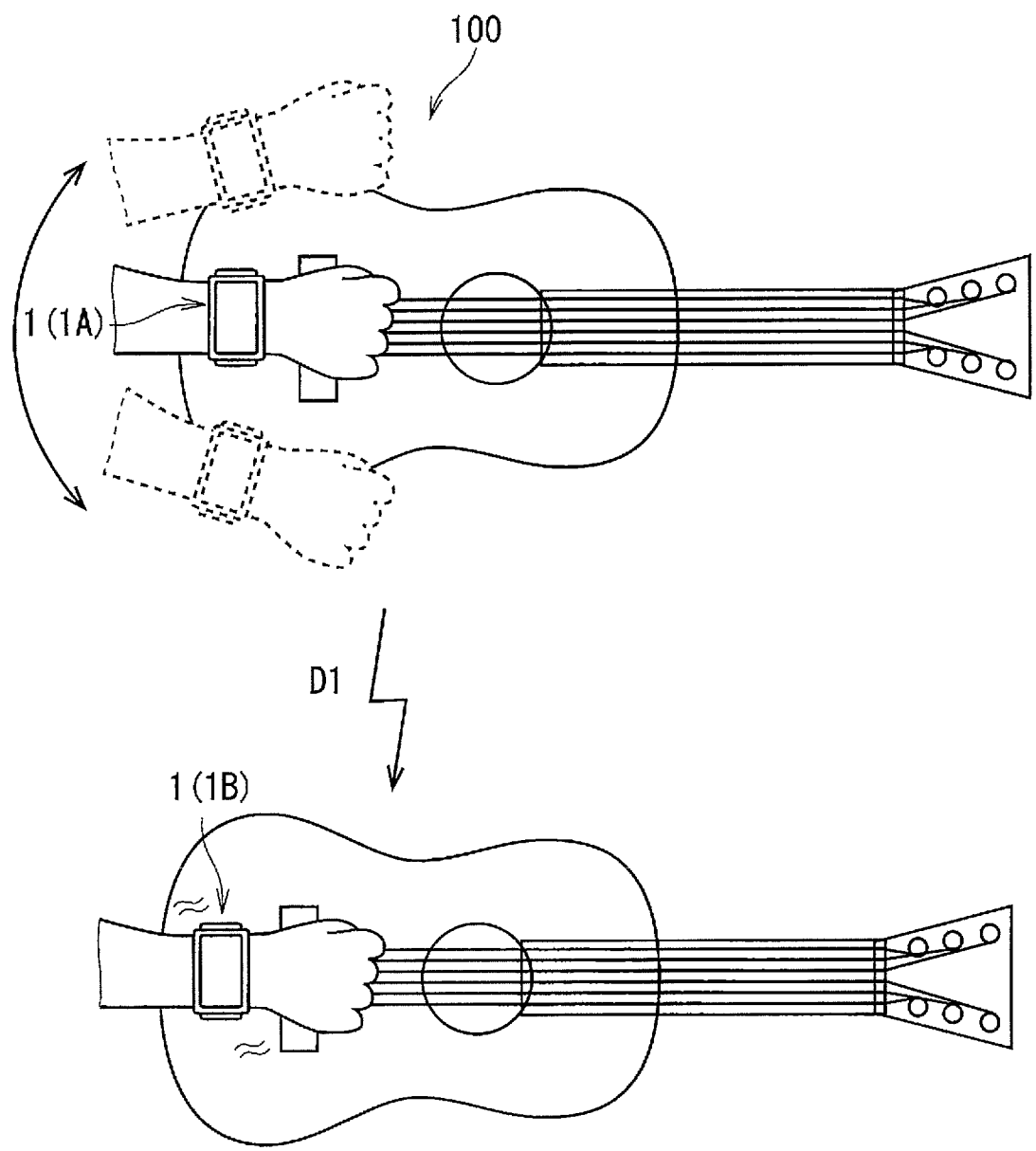
FIG. 22 schematically illustrates one example structure of a wearable apparatus system.

FIG. 21 illustrates a functional block diagram schematically showing one example electrical configuration of the wearable apparatus 1. FIG. 22 illustrates one example structure of the wearable apparatus system 100. The wearable apparatus 1 in FIG. 21 differs from that in FIG. 17 in regard to the sensor 26.

The sensor 26 may be, for example an accelerometer that detects acceleration of the wearable apparatus 1. For example, when the user moves the arm, the wearable apparatus 1 spatially moves. Here, the wearable apparatus 1 moves with acceleration. The sensor 26 can detect this acceleration, convert a value of the detected acceleration into an electrical signal, and output the electrical signal to the controller 21. The sensor 26 can detect acceleration based on a method, for example, a capacitive method, a piezo-resistive method, or a thermal detection method. This sensor 26 detects, for example, acceleration components on x, y, and z axes that are approximately orthogonal to one another.

The controller 21 can recognize the acceleration value based on the electrical signal entered from the sensor 26. A time integral of this acceleration indicates a moving velocity of the wearable apparatus 1, and a time integral of the moving velocity indicates a position (or an amount of movement) of the wearable apparatus 1. Thus, the controller 21 can recognize the spatial movement of the wearable apparatus 1 based on the acceleration.

As illustrated in FIG. 22, when the user UA, for example, perpendicularly periodically moves the arm, the wearable apparatus 1A is reciprocated. Such a movement is performed when, for example, the user plays an instrument. When the user plays, for example, the guitar or the bass, the user moves the arm up and down to pluck the strings thereof. When the user plays, for example, the drums, the user moves the arms up and down to beat the drums.

The transmission/reception processor 201 transmits, to the other wearable apparatus 1, the physical information based on the acceleration. The time-series data on the acceleration can be adopted as the physical information based on movement. Conversely, the transmission/reception processor 201 receives, from the other wearable apparatus 1, the physical information based on the acceleration of the other wearable apparatus 1.

The stimulus processor 202 causes the vibrator 233 to vibrate based on the physical information so that, for example, the rhythm of movement of the wearable apparatus 1 should be reproduced on the sense organs in the user's skin. The stimulus processor 202, for example, detects a period of movement of the other wearable apparatus 1 based on the physical information. The stimulus processor 202 may detect the period, for example, based on the timing with which the acceleration takes a peak value or a bottom value.

Then, the stimulus processor 202 causes the vibrator 233 to vibrate with the period. The stimulus processor 202 causes the vibrator 233 to vibrate, for example, with the timing over a shorter period of time. Consequently, the vibrator 233 can vibrate at the rhythm of the movement of the other wearable apparatus 1. FIG. 22 schematically illustrates the vibration of the wearable apparatus 1B with four wave lines.

The user UB can sense the rhythm of the movement of the arm of the user UA through the vibration of the vibrator 233B at the rhythm of the movement of the arm of the user UA. For example, when the user UA plays the guitar, the user UB can sense the movement of the arm. Thus, the user UB can practice the guitar based on this sensation.

For example, the vibrator 233 may vibrate with the timing of plucking the strings for the user UB to practice the guitar. This is because the vibration makes it easier for the user UB to understand the timing of plucking the strings. When the user UA plucks the strings, the acceleration can be considered as small. Thus, the stimulus processor 202B of the wearable apparatus 1B may cause the vibrator 233 to vibrate with the timing with which the acceleration of the wearable apparatus 1A takes the bottom value.

The transmission/reception processor 201A of the wearable apparatus 1A may transmit the physical information based on the acceleration only if the wearable apparatus 1A is reciprocated by the user. Whether the wearable apparatus 1A is reciprocated can be determined based on, for example, the time-series data on the acceleration detected by the sensor 26A. The transmission/reception processor 201A can determine that the wearable apparatus 1A is reciprocated, for example, if the acceleration periodically varies between the peak value and the bottom value over a predetermined duration. Thus, transmission of the unnecessary physical information can be reduced.

Figure 23:
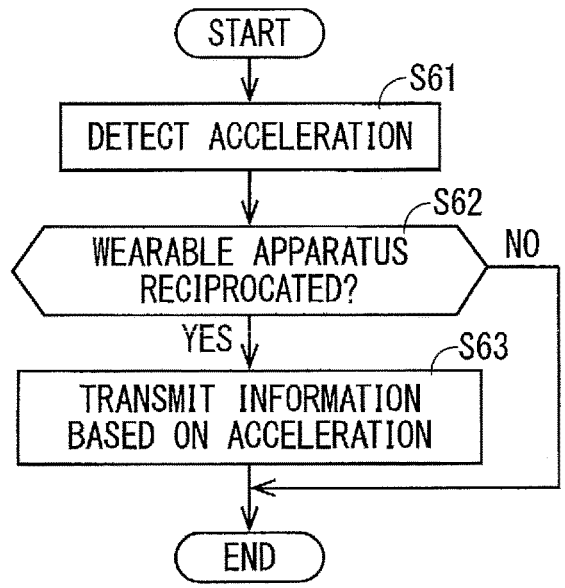
FIG. 23 illustrates a flowchart showing one example of operations of a wearable apparatus.
Figure 24:
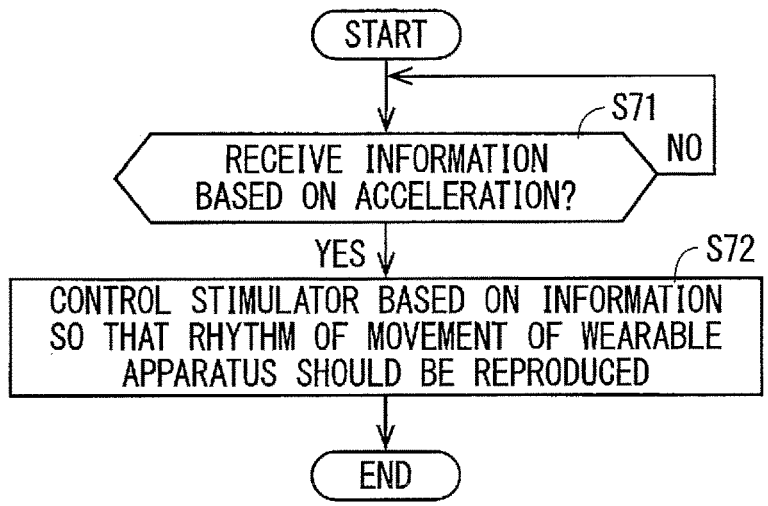
FIG. 24 illustrates a flowchart showing one example of operations of a wearable apparatus.

FIGS. 23 and 24 illustrate flowcharts showing examples of operations of the wearable apparatuses 1A and 1B, respectively. A series of the operations in each of FIGS. 23 and 24 may be repeated, for example, at predetermined time intervals. With reference to FIG. 23, the sensor 26A detects acceleration, and outputs a result of the detection to the controller 21A in Step S61. Next in Step S62, the transmission/reception processor 201A determines whether the wearable apparatus 1A is reciprocated, based on the time-series data on the acceleration detected by the sensor 26A. If a positive determination is made, the transmission/reception processor 201A transmits physical information based on the acceleration (for example, the time-series data on the acceleration) to the wearable apparatus 1B through the wireless communication unit 22A in Step S63. On the other hand, if a negative determination is made in Step S62, the controller 21A ends the processes. The controller 21 may execute Step S63 without executing Step S62.

With reference to FIG. 24, the transmission/reception processor 201B determines whether to have received the physical information based on the acceleration through the wireless communication unit 22B in Step S71. If determining no reception of the physical information, the transmission/reception processor 201B executes Step S71 again. If determining the reception of the physical information, in Step S72, the stimulus processor 202B causes, for example, the vibrator 233 to vibrate based on the physical information as described above so that the rhythm of the movement of the wearable apparatus 1A should be reproduced.

The physical information is not limited to the time-series data on the acceleration. The transmission/reception processor 201 may transmit, as the physical information, for example, information indicating the timing with which the acceleration takes the peak value or information indicating the period of the acceleration. Then, in the wearable apparatus 1 after receipt of the information, the stimulus processor 202 may cause the stimulator 23 to stimulate the user's skin with the period. In other words, the transmission/reception processor 201A may transmit information necessary for causing the stimulator 23 to stimulate the sense organs in the user's skin at the rhythm of the movement of the wearable apparatus 1.

[Intensity of Sound of Guitar]

The stimulator 23 may comprise, for example, the band part 3 and the tightening mechanism 231. This stimulator 23 can tighten the arm of the user with a controllable tightening force. Here, it is intended to reproduce, with this tightening force, the intensity of plucking the strings of the guitar by the user.

The sensor 26 comprises not only the accelerometer but, for example, a force sensor. The force with which the strings are plucked is conveyed to the arm of the user, and detected by the force sensor. For example, when the user strongly plucks the strings of the guitar, the force sensor detects the larger force. Then, the transmission/reception processor 201A of the wearable apparatus 1A may transmit, to the wearable apparatus 1B, physical information in which the acceleration is associated with the force, where the acceleration and the force are detected by the sensor 26A.

Figure 25:
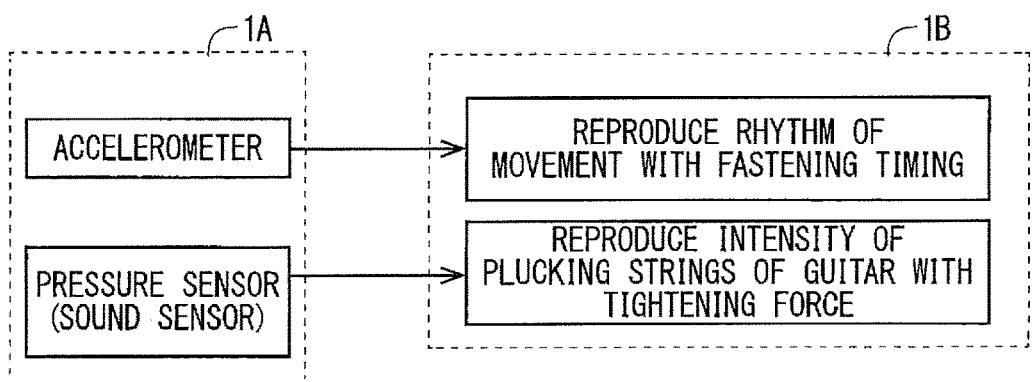
FIG. 25 illustrates a reproduction method corresponding to each sensor.

The stimulus processor 202B in the wearable apparatus 1B reproduces the intensity based on the force detected by the force sensor as well as reproducing the rhythm of the movement of the wearable apparatus 1A based on the acceleration detected by the accelerometer. FIG. 25 illustrates a reproduction method corresponding to each sensor. The stimulus processor 202B causes the tightening mechanism 231 to tighten a worn portion of the wearable apparatus 1A with the period of movement of the wearable apparatus 1A based on the time-series data on the acceleration and with the tightening force based on the detected force.

The intensity of plucking the strings of the guitar may be determined by the volume of sound. Specifically, the sensor may comprise a sound sensor as a replacement for the force sensor. The sound sensor is, for example, a microphone. The sound sensor converts the sound entered from outside into a sound signal and outputs the sound signal to the controller 21. The controller 21 can find the volume of the sound based on this sound signal. When the user strongly plucks the strings of the guitar, the sound sensor detects the larger sound.

The sensor 26 may comprise only the force sensor without the accelerometer. This is because this force sensor detects the force with the timing of plucking the strings and thus can understand the timing of plucking the strings based on the detection of the force sensor. For example, the transmission/reception processor 201A transmits the time-series data on the force detected by the sensor 26 as the physical information. The stimulus processor 202B may cause, based on the time-series data on the force with the timing with which the force takes a peak value, the tightening mechanism 231 to tighten the arm of the user with the tightening force corresponding to the peak value.

[Example of Periodical Movement of Electronic Apparatus 1]

[Vibration]

When the arms of the user UA shiver with, for example, cold or sickness, this contributes to the periodical movement (or vibrations) of the wearable apparatus 1A. Even in such a case, the wearable apparatus 1A transmits the physical information based on the acceleration to the wearable apparatus 1B. Then, the stimulus processor 202B of the wearable apparatus 1B causes the vibrator 233B to vibrate so that the rhythm of movement of the wearable apparatus 1A should be reproduced. The stimulus processor 202B of the wearable apparatus 1B may, for example, cause the vibrator 233B to vibrate for each period of the acceleration over a shorter period of time. Thus, the user UB can sense the shivering of the user UA. Thus, the user UB can take an appropriate action. The user UB can, for example, make contact with the user UA or pick up the user UA.

[Running]

Figure 26:
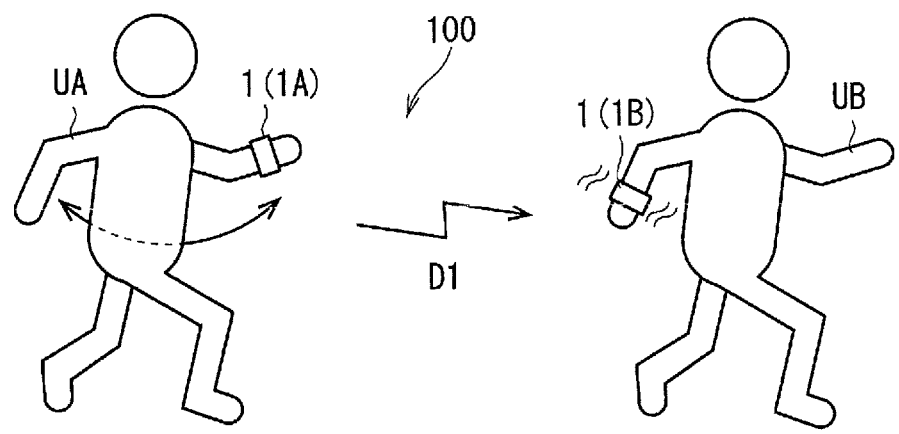
FIG. 26 schematically illustrates one example structure of a wearable apparatus system.

FIG. 26 illustrates one example structure of the wearable apparatus system 100. As illustrated in FIG. 26, for example, even when the user UA is running, the wearable apparatus 1A is periodically moved. This is because the user UA is running with the arms swinging.

Even in such a case, the wearable apparatus 1A transmits the physical information based on the acceleration to the wearable apparatus 1B. Then, the stimulus processor 202B of the wearable apparatus 1B causes the vibrator 233B to vibrate so that the rhythm of movement of the wearable apparatus 1A should be reproduced. The stimulus processor 202B of the wearable apparatus 1B may, for example, cause the vibrator 233B to vibrate for each period of the acceleration over a shorter period of time. The user UB can sense the rhythm of the swinging arms of the user UA. Thus, the user UB can guess the pace of the running of the user UA, and virtually compete with the user UA.

[System]

Figure 27:
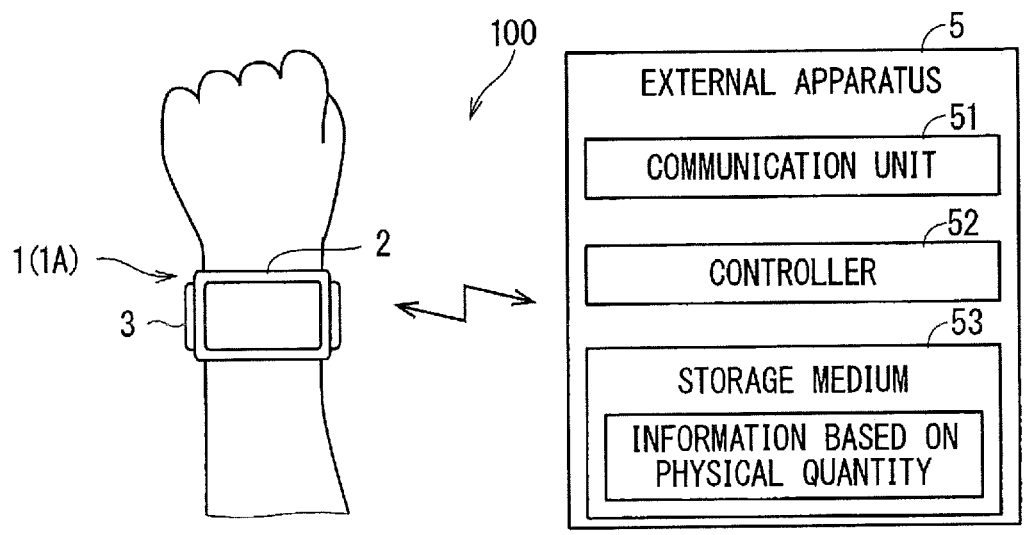
FIG. 27 schematically illustrates one example structure of a wearable apparatus system.

FIG. 27 illustrates one example structure of the wearable apparatus system 100. FIG. 27 exemplifies that the wearable apparatus 1 can communicate with an external apparatus 5. The external apparatus 5 comprises, for example, a communication unit 51, a controller 52, and a storage medium 53. The communication unit 51 can transmit and receive a signal to and from the wearable apparatus 1 directly or through another apparatus.

The physical information based on the physical quantity is stored in the storage medium 53. For example, the transmission/reception processor 201 of the wearable apparatus 1 transmits, to the external apparatus 5, physical information based on the physical quantity detected by the sensor 26. The controller 52 receives this physical information through the communication unit 51, and stores this in the storage medium 53. In other words, the physical information generated by the wearable apparatus 1 in the past is stored in the storage medium 53 as log information.

Next, the technology for reproducing the physical quantity detected by the wearable apparatus 1 in the past, based on the physical information stored in this storage medium 53 will be described.

The transmission/reception processor 201 can transmit a request signal for requesting the physical information to the external apparatus 5 through the wireless communication unit 22. For example, the input unit 24 may receive an input triggering transmission of this request signal. Here, the transmission/reception processor 201 transmits the request signal in response to the input from the user.

Upon receipt of this request signal, the controller 52 reads the physical information stored in the storage medium 53, and transmits the physical information to the wearable apparatus 1.

The transmission/reception processor 201 receives the physical information, and the stimulus processor 202 controls the stimulator 23 so that the physical quantity should be reproduced on the sense organs of the user. Consequently, the physical quantity stored in the external apparatus 5 can be reproduced using the physical information based on the physical quantity. Thus, the physical quantity can be reproduced with the timing different from that with which the physical quantity has been detected.

For example, the wearable apparatus 1A may transmit, to the external apparatus 5, the physical information based on the acceleration detected while the user UA was running. The controller 52 may store the physical information in the storage medium 53. For example, the time-series data on the acceleration detected during the running can be used as the physical information.

For example, upon start of running in another day, the user UA enters an instruction for transmitting a request signal to the wearable apparatus 1A. Consequently, the wearable apparatus 1A vibrates at the rhythm of the swinging arms in the previous running. Thus, the user UA can run while sensing the pace of the previous running.

Alternatively, the wearable apparatus 1A may transmit, to the external apparatus 5, the physical information based on the acceleration detected while the user UA was playing the guitar. The controller 52 may store the physical information in the storage medium 53. For example, the time-series data on the acceleration detected during playing the guitar can be used as the physical information.

When practicing the guitar, the user UB enters an instruction for transmitting a request signal to the wearable apparatus 1B. Consequently, the wearable apparatus 1B vibrates at the rhythm of the swinging arm of the user UA during playing the guitar. Thus, the user UB can practice the guitar while sensing the rhythm of the swinging arm of the user UA. Consequently, the user UB can set the practicing time at any time, without any need for practicing the guitar while the user UA is playing the guitar.

[Current Position]

Figure 28:
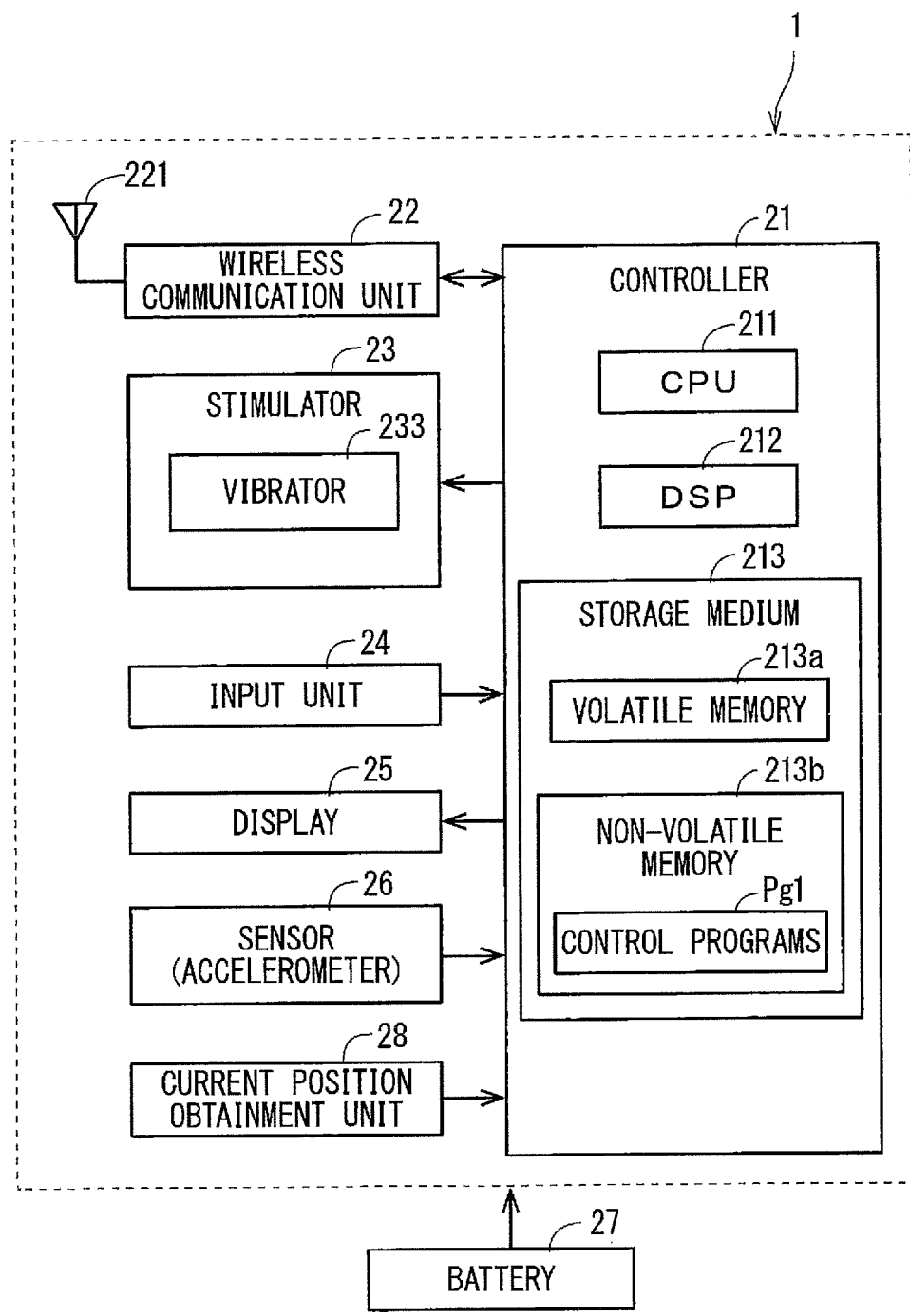
FIG. 28 illustrates a functional block diagram schematically showing one example electrical configuration of a wearable apparatus.

FIG. 28 illustrates a functional block diagram schematically showing one example electrical configuration of the wearable apparatus 1. The wearable apparatus 1 in FIG. 28 differs from that in FIG. 21 by the presence or absence of a current position obtainment unit 28.

The current position obtainment unit 28 can obtain the current position of the wearable apparatus 1 and output the position information to the controller 21. The current position obtainment unit 28 comprises, for example, a position information receiver. This position information receiver receives a signal from an artificial satellite and calculates the current position based on the signal. The position information indicating the current position includes latitude information and longitude information. Examples of such positioning system include the Global Positioning System (GPS), the Global Navigation Satellite System (GLONASS), GALILEO, COMPASS, the Indian Regional Navigational Satellite System (IRNSS), and the Quasi-Zenith Satellite System (QZSS).

Alternatively, if the wireless communication unit 22 can communicate with a base station, the current position obtainment unit 28 may calculate the current position of the wearable apparatus 1 based on a base station capable of communication. A communication coverage area in which communication is possible is set to each base station. If the wireless communication unit 22 can communicate with a base station, it is clear that the wearable apparatus 1 is located in the communication coverage area of the base station. If the wireless communication unit 22 can communicate with a plurality of base stations, it is clear that the wearable apparatus 1 is located in a region where communication coverage areas of the plurality of base stations overlap. Thus, the current position obtainment unit identifies the base stations capable of communication with the wireless communication unit 22, and calculates the current position based on these. Here, the current position obtainment unit 28 may be implemented as one function of the controller 21.

The controller 21 associates information based on the acceleration detected by the sensor 26 with the position information obtained by the current position obtainment unit 28. When, for example, the user is running, the sensor 26 repeatedly detects the acceleration, and the current position obtainment unit 28 repeatedly obtains the position information. The controller 21 may, for example, associate position information obtained with the timing that is the closest to the timing with which an acceleration has been detected, with the acceleration. This holds true for the other accelerations.

The transmission/reception processor 201 may transmit, to the external apparatus 5, the physical information based on the acceleration and the position information. For example, an acceleration, a position, and information indicating the correspondence between these can be used as the physical information. The controller 52 of the external apparatus 5 stores this physical information in the storage medium 53.

Figure 29:
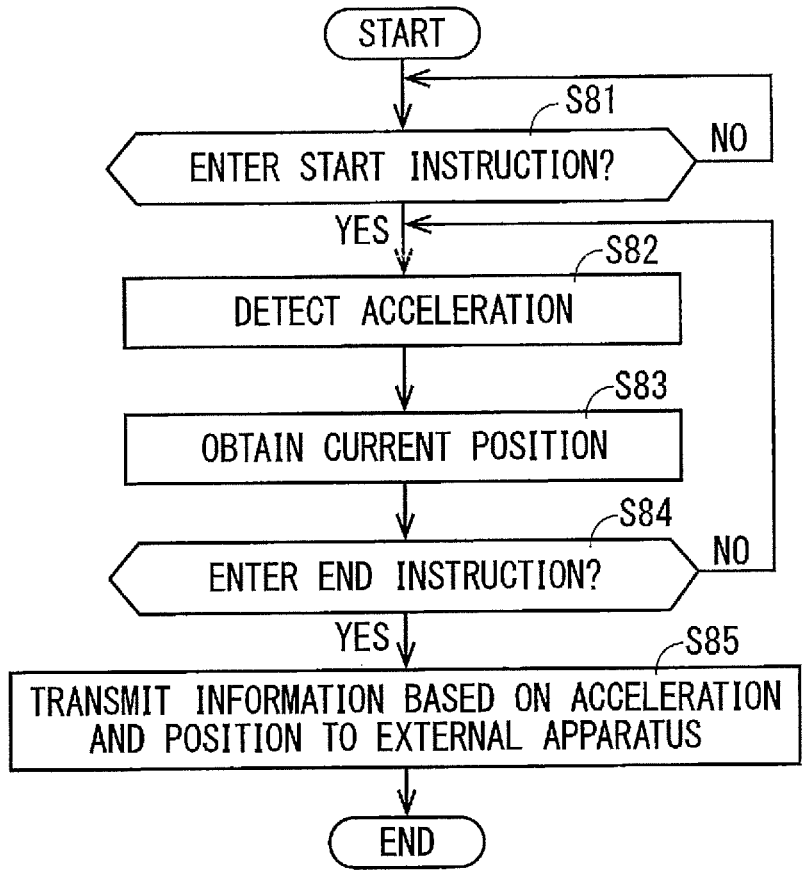
FIG. 29 illustrates a flowchart showing one example of operations of a wearable apparatus.

FIG. 29 illustrates a flowchart showing one example of the operations of the wearable apparatus 1. FIG. 29 exemplifies that the controller 21 determines whether the user enters a start instruction to the input unit 24 in Step S81. This start instruction functions as a trigger to start detecting this acceleration and obtain the current position. The user starts running around the same time as entering this start instruction. If determining that this start instruction is not entered, the controller 21 executes Step S81 again.

If the controller 21 determines that this start instruction has been entered, the sensor 26 detects the acceleration in Step S82. Then in Step S83, the current position obtainment unit 28 obtains the current position. An order for performing Steps S82 and S83 may be reversed. Steps S82 and S83 may be performed in parallel.

Next in Step S84, the controller 21 determines whether the user enters an end instruction to the input unit 24. This end instruction functions as a trigger to transmit the physical information based on the acceleration and the position. If determining that this end instruction is not entered, the controller 21 executes Step S82 again. If determining that the end instruction has been entered, the controller 21 generates the physical information by associating the acceleration with the current position, and transmits the physical information to the external apparatus 5 in Step S85.

Figure 30:
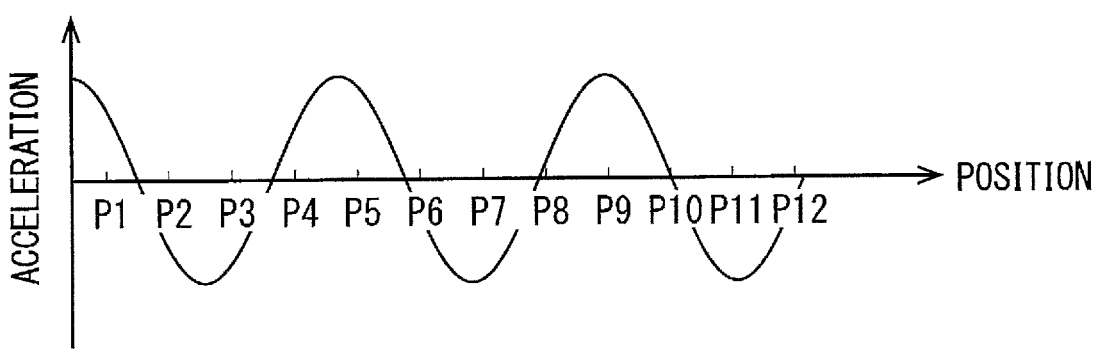
FIG. 30 schematically illustrates one example relationship between positions and accelerations.

In the one example of the operations, the physical information when the user was running in the past is stored in the storage medium 53 of the external apparatus 5 as log information. FIG. 30 schematically illustrates one example relationship between positions and accelerations. Since the user moves with the arms swinging in the running, the acceleration periodically varies using the position as a variable. FIG. 30 schematically exemplifies the accelerations represented by sinusoidal waves using the positions as variables. Although FIG. 30 illustrates the accelerations continuously, the accelerations may be discrete values as the physical information.

Next, the technology for reproducing the rhythm of the swinging arms in the past running, based on the physical information stored in this storage medium 53 will be described.

The transmission/reception processor 201 can transmit a request signal for requesting the physical information based on the acceleration and the position that are stored in the external apparatus 5. For example, the input unit 24 may receive an input triggering transmission of this request signal. Here, the transmission/reception processor 201 transmits the request signal in response to the input from the user.

Upon receipt of this request signal, the controller 52 reads the physical information stored in the storage medium 53, and transmits the physical information to the wearable apparatus 1.

The transmission/reception processor 201 receives this physical information. This physical information includes a position (hereinafter will be referred to as a past position) and an acceleration. The stimulus processor 202 calculates a period of movement of the wearable apparatus 1 in the past position, based on the physical information. For example, the stimulus processor 202 may calculate, as the period with reference to FIG. 30, a duration from the first timing with which the acceleration takes the peak value to the second timing with which the acceleration takes the next peak value. This period is a period common to a plurality of past positions (e.g., past positions P1 to P4 in FIG. 30) obtained from the first timing to the second timing. In other words, one period is calculated for a plurality of the past positions P1 to P4 in common that are obtained during a duration from the first timing to the second timing. The stimulus processor 202 can calculate a period in association with all the past positions by repeatedly performing these processes. In the example of FIG. 30, one period is calculated for the past positions P1 to P4, one period is calculated for the past positions P5 to P9, and one period is calculated for the past positions P10 to P12.

Then, the stimulus processor 202 determines whether a difference between the current position obtained by the current position obtainment unit 28 and a past position is smaller than a position reference value. In other words, the stimulus processor 202 determines whether the current position almost coincides with the past position. This position reference value may be, for example, preset and stored in the storage medium 213. If determining that the difference is smaller than the position reference value, the stimulus processor 202 causes the stimulator 23 to stimulate the sense organs in the user's skin with a period corresponding to the past position so that the rhythm of movement of the wearable apparatus 1 in the past position is reproduced on the sense organs. The stimulus processor 202, for example, causes the vibrator 233 to vibrate with the period corresponding to the past position.

Figure 31:
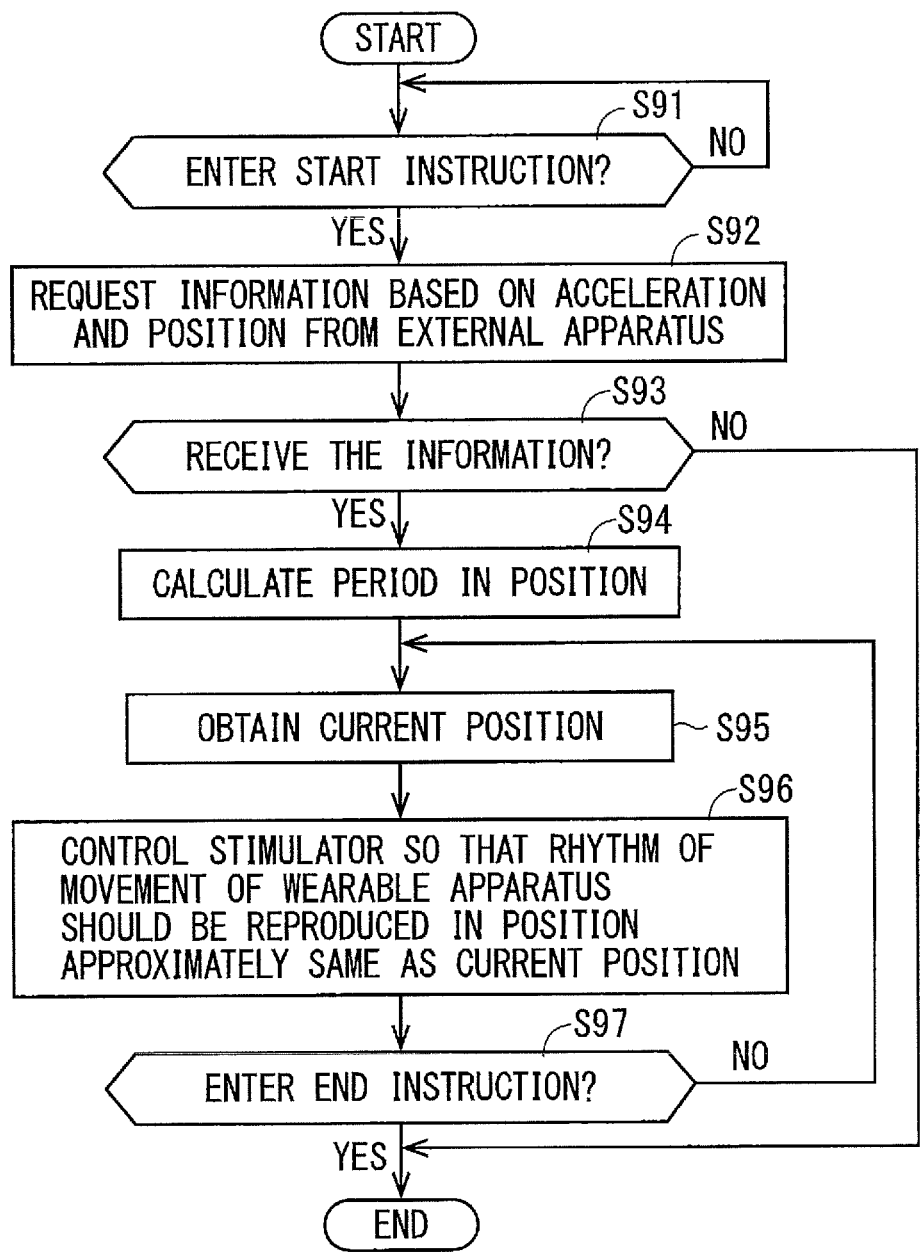
FIG. 31 illustrates a flowchart showing one example of operations of a wearable apparatus.

FIG. 31 illustrates a flowchart showing one example of the operations of the wearable apparatus 1. FIG. 31 exemplifies that the controller 21 determines whether the user enters the second start instruction to the input unit 24 in Step S91. This second start instruction functions as a trigger to start reproducing the rhythm of movement of the wearable apparatus 1 (the swinging arms of the user) in the past running. The user starts running around the same time as the input of this second start instruction. If determining that this second start instruction is not entered, the controller 21 executes Step S91 again.

If the controller 21 determines that the second start instruction has been entered, the transmission/reception processor 201 requests the physical information based on the acceleration and the position from the external apparatus 5 in Step S92. Next in Step S92, the transmission/reception processor 201 determines whether to have received this physical information. The transmission/reception processor 201 determines no reception of the physical information, for example, if not receiving the physical information for a predetermined duration. If determining no reception of the physical information, the controller 21, for example, ends the processes.

If determining reception of the physical information, the controller 21 calculates a period in the past position based on the physical information in Step S94. Next in Step S95, the current position obtainment unit 28 obtains the current position. Next in Step S96, the stimulus processor 202 controls the stimulator 23 so that the rhythm of the past movement of the wearable apparatus 1 should be reproduced in a position approximately the same as the current position (a position where a difference with the current position is smaller than the position reference value). The stimulus processor 202 causes the vibrator 233 to vibrate, for example, with the period corresponding to the past position. Next in Step S97, the controller 21 determines whether the user enters the second end instruction to the input unit 24. The second end instruction functions as a trigger to end reproduction of the rhythm of movement of the wearable apparatus 1 in the past running. If determining that the second end instruction is not entered, the current position obtainment unit 28 executes Step S95 again. If determining that the second end instruction has been entered, the controller 21 ends the processes.

Thus, the user UA can run while sensing the rhythm of the swinging arms in the position in the past running. Thus, the user UA can guess the pace of the past running in the position and virtually compete with the user in the past.

[Plurality of Pieces of Physical Information]

For example, when the user runs through the same route at predetermined intervals (e.g., every day) and the wearable apparatus 1 operates accordingly, the physical information is recorded in the storage medium 53 of the external apparatus 5 each time the user runs.

Here, the wearable apparatus 1 may receive such plurality of pieces of physical information from the external apparatus 5. The controller 21 calculates a period corresponding to a past position for each of the pieces of the physical information. The controller 21 may calculate, as the period corresponding to the past position, a statistic of a plurality of periods (e.g., a statistic such as an average, the maximum value, or the minimum value). The controller 21 can calculate the period corresponding to each past position by performing this process on all the past positions.

Which statistic (e.g., an average, the maximum value, or the minimum value) is adopted may be preset. A statistic corresponding to an input of the user may be adopted.

[Tightening Mechanism]

Figure 32:
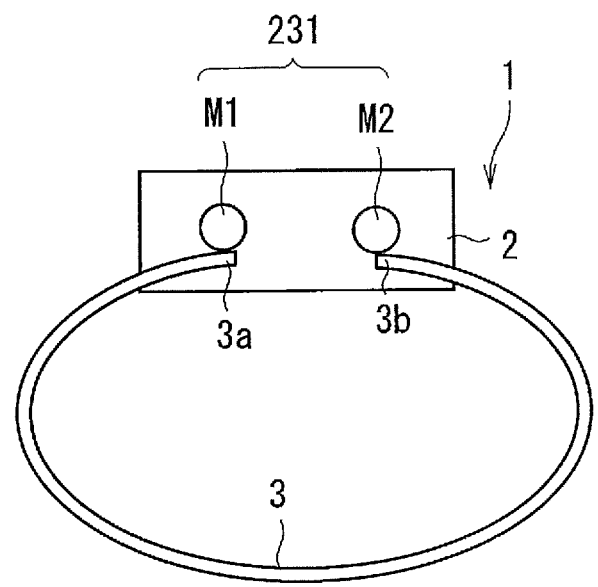
FIG. 32 schematically illustrates one example structure of a wearable apparatus.

FIG. 32 schematically illustrates one example structure of the wearable apparatus 1. The tightening mechanism 231 of the wearable apparatus 1 in FIG. 32 comprises two motors M1 and M2 in comparison with the wearable apparatus 1 in FIG. 4. The motors M1 and M2 are rotated under the control of the controller 21. The end 3a of the band part 3 is fixed to the motor M1, and the other end 3b is fixed to the motor M2. Thus, rotation of the motors M1 and M2 enables the motor M1 and the motor M2 to wind portions of the band part 3 on the end 3a side and the other end 3b side, respectively.

Figure 33:
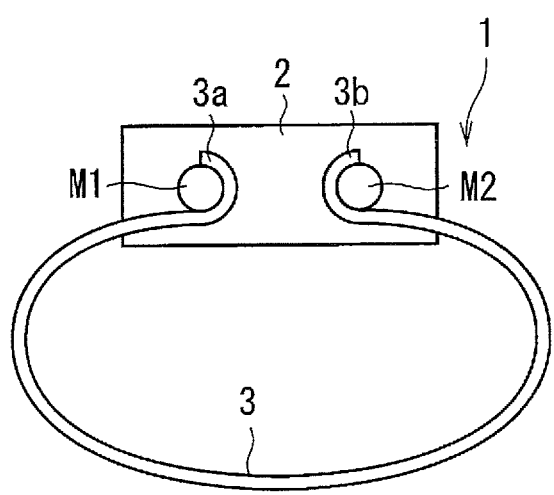
FIG. 33 schematically illustrates one example structure of a wearable apparatus.

FIG. 33 schematically illustrates one example structure of the wearable apparatus 1. FIG. 33 exemplifies that portions of the band part 3 are wound around the two motors M1 and M2. In other words, the band part 3 is wound by the two motors M1 and M2. Thus, the perimeter of the portion of the band part 3 that extends from the main body 2 is shorter than that of the wearable apparatus 1 in FIG. 32. In other words, the two motors M1 and M2 wind the portions of the band part 3 on the end 3a side and the other end 3b side, respectively, so that the band part 3 can tighten the arm of the user. The controller 21 can control the tightening force by controlling, for example, output torque of these motors M1 and M2.

Conversely, rotation of the motors M1 and M2 in a direction opposite to that for tightening increases the perimeter of the portion of the band part 3 that extends from the main body 2. Consequently, the motors M1 and M2 can loosen the tightening of the arm by the band part 3.

Figure 34:
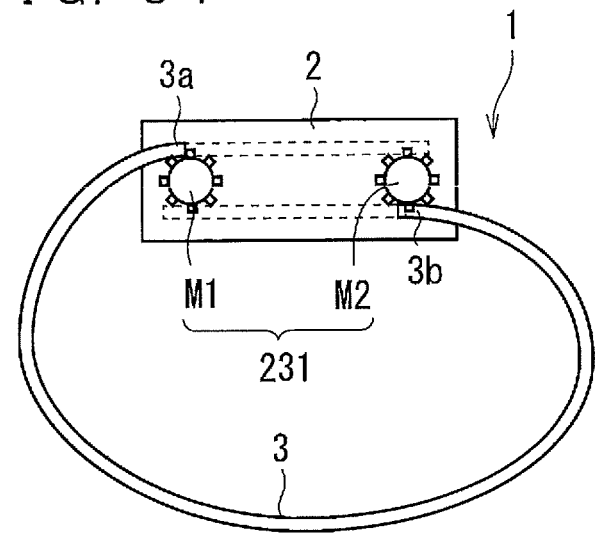
FIG. 34 schematically illustrates one example structure of a wearable apparatus.

FIG. 34 schematically illustrates one example structure of the wearable apparatus 1. FIG. 34 exemplifies that the tightening mechanism 231 comprises the motors M1 and M2. The motors M1 and M2 are rotated under the control of the controller 21. A plurality of protrusions are erected around each of the motors M1 and M2 along the circumferential direction. In other words, the motors M1 and M2 are shaped like cogs when viewed along the rotation axis. On the other hand, a plurality of depressions are formed, along the longitudinal direction, on the inner peripheral surface of the band part 3 on the end 3a side and on the outer peripheral surface of the band part 3 on the other end 3b side. The depressions of the band part 3 on the end 3a side are engaged in the protrusions of the motor M1. The depressions of the band part 3 on the other end 3b side are engaged in the protrusions of the motor M2.

Figure 35:
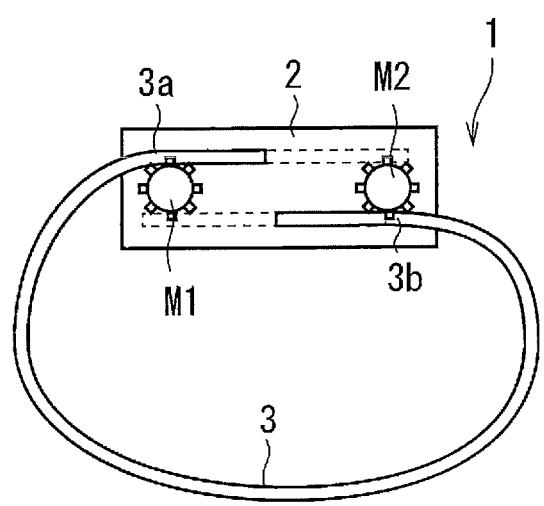
FIG. 35 schematically illustrates one example structure of a wearable apparatus.

The rotation of these motors M1 and M2 enables the end 3a and the other end 3b of the belt part 3 to move inside the main body 2 under the principles similar to those of the conveyor belt. FIG. 35 schematically illustrates one example structure of the wearable apparatus 1. The end 3a and the other end 3b of the band part 3 in the wearable apparatus 1 in FIG. 35 are located more inside the main body 2 than those in FIG. 34. Thus, the perimeter of the portion of the band part 3 that extends from the main body 2 is shorter than that of the wearable apparatus 1 in FIG. 34. Thus, the band part 3 can tighten the arm of the user. The controller 21 can control the tightening force by controlling, for example, output torque of these motors M1 and M2.

Conversely, rotation of the motors M1 and M2 in a direction opposite to that for tightening increases the perimeter of the portion of the band part 3 that extends from the main body 2. Consequently, the motors M1 and M2 can loosen the tightening of the arm by the band part 3.

In the main body 2 illustrated in FIGS. 34 and 35, regions enclosed by broken lines indicate the space into which the band part 3 can be inserted in the longitudinal direction.

Figure 36:
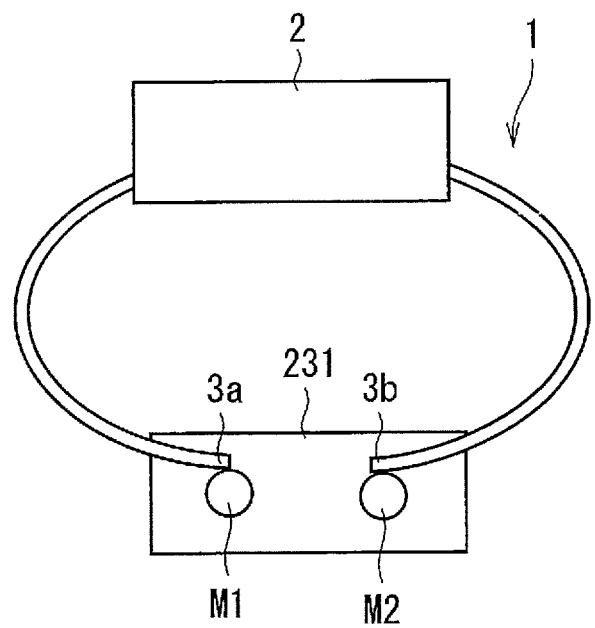
FIG. 36 schematically illustrates one example structure of a wearable apparatus.
Figure 37:
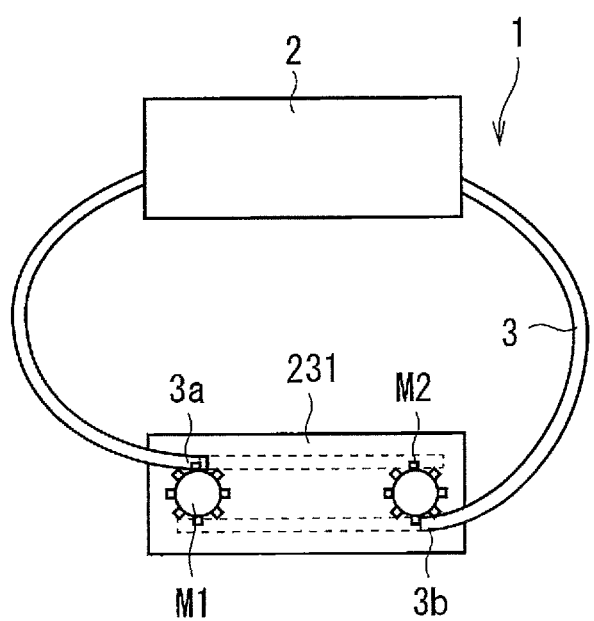
FIG. 37 schematically illustrates one example structure of a wearable apparatus.

FIGS. 36 and 37 each schematically illustrate one example structure of the wearable apparatus 1. FIGS. 36 and 37 each exemplify the tightening mechanism 231 disposed outside the main body 2. The tightening mechanism 231 is disposed, for example, to face the main body 2. In other words, the tightening mechanism 231 is located opposite to the main body 2 with respect to the center of the ring formed in the wearable apparatus 1. The specific structure of the tightening mechanism 231 in FIG. 36 is the same as that in FIG. 32, and the specific structure of the tightening mechanism 231 in FIG. 37 is the same as that in FIG. 34. Thus, the repeated description will be avoided.

Although the wearable apparatus 1 is described in detail as above, the foregoing description is in all aspects illustrative and does not restrict this disclosure. The various modifications described above are applicable in combination unless any contradiction occurs. It is understood that numerous modifications that have not yet been exemplified can be devised without departing from the scope of this disclosure.

What is claimed is:

1. A wearable apparatus worn on a first user, the wearable apparatus comprising:
a first communication unit configured to receive first information based on a physical quantity;
a stimulator configured to stimulate sense organs in the skin of the first user by a controllable stimulation quantity;
at least one first processor configured to cause the stimulator to stimulate the sense organs based on the first information so that the physical quantity is reproduced on the sense organs;
a first sensor configured to repeatedly detect an acceleration;
a position obtainment unit configured to repeatedly obtain a position of the wearable apparatus; and
an input unit,
wherein the at least one first processor:
transmits, as the first information, information in which the physical quantity is associated with the position to an external apparatus through the first communication unit to cause the external apparatus to store the first information as log information;
obtains the first information from the external apparatus in response to an input to the input unit;
calculates, based on the first information, a period of past spatial movement of the wearable apparatus in each position included in the first information;
determines whether a difference between a current position obtained by the position obtainment unit and each of the positions in the first information is less than a predetermined threshold; and
causes the stimulator to stimulate the sense organs of the first user based on the physical quantity associated with the period corresponding to the current position if determining that the difference is less than the predetermined threshold.

2. The wearable apparatus according to claim 1,
wherein the physical quantity includes a physical quantity perceivable by the sense organs.

3. The wearable apparatus according to claim 2,
wherein the physical quantity comprises a force,
the stimulator comprises:
a first band part; and
a first tightening mechanism configured to tighten, using the first band part, a portion of the body of the first user with a controllable tightening force, and
the at least one first processor causes the first tightening mechanism to tighten the portion of the body of the first user based on the first information so that the force is reproduced by the tightening force.

4. A wearable apparatus system, comprising:
the wearable apparatus according to claim 3; and
a second wearable apparatus comprising:
a second communication unit capable of communication with the first communication unit;
a second sensor configured to detect the force as the physical quantity; and
at least one second processor configured to transmit, to the wearable apparatus through the second communication unit, information based on the force detected by the first sensor as the first information.

5. The wearable apparatus system according to claim 4,
wherein the at least one first processor transmits, to the second wearable apparatus through the first communication unit, second information based on the force detected by the second sensor, and
the second wearable apparatus further comprises:
a second band part; and
a second tightening mechanism configured to tighten, using the second band part, a second user with a controllable tightening force; wherein
the at least one second processor is configured to receive the second information through the second communication unit and cause the second tightening mechanism to tighten the second band part based on the second information so that the force detected by the second sensor is reproduced.

6. The wearable apparatus according to claim 2,
wherein the physical quantity comprises a temperature,
the stimulator comprises a thermal element configured to generate or absorb controllable heat, and
the at least one first processor controls the thermal element based on the first information so that the temperature is reproduced.

7. The wearable apparatus according to claim 6,
wherein the physical quantity comprises temperatures at a plurality of positions,
the thermal element comprises a plurality of thermal elements, and
the at least one first processor controls the plurality of thermal elements so that a distribution of the temperatures is reproduced.

8. A wearable apparatus system, comprising:
the wearable apparatus according to claim 6; and
a second wearable apparatus comprising:
a second sensor configured to detect the temperature; and
a second communication unit configured to transmit, to the wearable apparatus, information based on the temperature as the first information.

9. The wearable apparatus according to claim 1,
wherein the physical quantity periodically varies, and
the at least one first processor causes the stimulator to stimulate the sense organs with a period of the physical quantity based on the first information.

10. The wearable apparatus according to claim 9,
wherein the stimulator comprises:
a band part; and
a tightening mechanism configured to tighten, using the band part, a portion of the body of the first user with a controllable tightening force, and
the at least one first processor causes the tightening mechanism to tighten the portion of the body of the first user with the period of the physical quantity based on the first information.

11. The wearable apparatus according to claim 9,
wherein the stimulator comprises a vibrator, and
the at least one first processor causes the vibrator to vibrate with the period of the physical quantity based on the first information.

12. A wearable apparatus system, comprising:
the wearable apparatus according to claim 9; and
a second wearable apparatus comprising:
a second sensor configured to detect biological information that periodically varies; and
a second communication unit configured to transmit, to the wearable apparatus, information based on the biological information as the first information.

13. A wearable apparatus system, comprising:
the wearable apparatus according to claim 9; and
a second wearable apparatus comprising:
a second sensor configured to detect an acceleration; and a second communication unit configured to transmit, to the wearable apparatus, information based on the acceleration as the first information.

14. A method of stimulating sense organs in the skin of a user, comprising:
- receiving first information based on a physical quantity;
- stimulating the sense organs using a wearable apparatus worn by the user based on the first information so that the physical quantity is reproduced on the sense organs;
- repeatedly obtaining a position of the wearable apparatus;
- transmitting, as the first information, information in which the physical quantity is associated with the position to an external apparatus for storage in a memory therein;
- obtaining the first information from the external apparatus in response to an input provided to an input unit of the wearable apparatus;
- calculating, based on the first information, a period of past spatial movement of the wearable apparatus in each position included in the first information;
- determining whether a difference between a current position obtained by the position obtainment unit and each of the positions in the first information is less than a predetermined threshold; and
- stimulating the sense organs of the user based on the physical quantity associated with the period corresponding to the position if determining that the difference is less than the predetermined threshold.

* * * * *